（12） United States Patent
Sarkar

(10) Patent No.: US 8,877,452 B2
(45) Date of Patent: Nov. 4, 2014

(54) NITRITE-REDUCTASE (NIRB) AS POTENTIAL ANTI-TUBERCULAR TARGET AND A METHOD TO DETECT THE SEVERITY OF TUBERCULOSIS DISEASE

(71) Applicant: Dhiman Sarkar, Pune (IN)

(72) Inventor: Dhiman Sarkar, Pune (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 13/778,838

(22) Filed: Feb. 27, 2013

(65) Prior Publication Data

US 2014/0242626 A1 Aug. 28, 2014

(51) Int. Cl.
*G01N 33/569* (2006.01)
*C12Q 1/06* (2006.01)

(52) U.S. Cl.
CPC ........................................ *C12Q 1/06* (2013.01)
USPC ........................................................ 435/7.71

(58) Field of Classification Search
None
See application file for complete search history.

(56) References Cited

PUBLICATIONS

Sen, N.P., and Donaldson, B. "Improved colorimetric method for determining nitrate and nitrate in foods", Journal of Association of Official Analytical Chemists 1978, vol. 61, pp. 1389-1394.*
Sarkar, S., and Sarkar, D. "Potential Use of Nitrate Reductase as a Biomarker for the Identification of Active and Dormant Inhibitors", Journal of Biomolecular Screening, vol. 17, pp. 966-973.*
Khan, A., and Sarkar, D. "A simple whole cell based high throughput screening protocol using *Mycobacterium bovis* BCG for inhibitors against dormant and active tubercle bacilli", Journal of Microbiological Methods 2008, vol. 73, pp. 62-68.*
Virtanen, S., "A study of nitrate reduction by mycobacteria. The use of the nitrate reduction test in the identification of mycobacteria.", Acta Tuberc. Scand. Suppl., 48, (1960), 1-116.
Bogdan, C., "Reactive oxygen and reactive nitrogen intermediates in innate and specific immunity", Current Opinion in Immunology, 12, (2000), 64-76.
Bradford, M. M., "A rapid and Sensitive Method for the Quantitation of Microgram Quantities of Protein Utilizing the Principle of Protein-Dye Binding", Analytical Biochemistry, 72, (1976), 248-254.
Brown, G. C., et al., "Nitric oxide and mitochondrial respiration", Biochimica et Biophysica Acta, 1411, (1999), 351-369.

Clegg, S., et al., "The roles of the polytopic membrane proteins NarK, NarU and NirC in *Escherichia coli* K-12: two nitrate and three nitrite transporters", Molecular Microbiology, 44(1), (2002), 143-155.
Flesch, I. E., et al., "Mechanisms Involved in Mycobacterial Growth Inhibition by Gamma Interferon-Activated Bone Marrow Macrophages: Role of Reactive Nitrogen Intermediates", Infection and Immunity, 59(9), (1991), 3213-3218.
Irfan, S., "Rapid Detection of *Mycobacterium tuberculosis* in Sputum Samples by Microscopic Observation Methods", Infectious Diseases Journal of Pakistan, vol. 17, Issue. 01, (Jan.-Mar. 2008), 10-13.
Kelm, M., "Nitric oxide metabolism and breakdown", Biochimica et Biophysica Acta, 1411, (1999), 273-289.
Khan, A., et al., "Bactericidal activity of 2-nitroimiclazole against the active replicating stage of *Mycobacterium bovis* BCG and *Mycobacterium tuberculosis* with intracellular efficacy in THP-1 macrophages", International Journal of Antimicrobial Agents, 32(1), (2008), 40-45.
Layer, G., et al., "Structure and function of enzymes in heme biosynthesis", Protein Science, 19(6), (2010), 1137-1161.
Nyka, W., "Studies on the Effect of Starvation on Mycobacteria", Infection and Immunity, 9(5), (1974), 843-850.
Sengupta, S., et al., "Purification and characterization of assimilatory nitrite reductase from *Candida utilis*", Biochem. J., 317, (1996), 147-155.
Shao, Z., et al., "Identification and functional analysis of a nitrate assimilation operon nasACKBDEF from *Amycolatopsis mediterranei* U32", Arch. Microbiol., 193, (2011), 463-477.
Sohaskey, C. D., et al., "Role of narK2X and narGHJI in Hypoxic Upregulation of Nitrate Reduction by *Mycobacterium tuberculosis*", Journal of Bacteriolo, 185(24), (2003), 7247-7256.
Stuehr, D. J., "Mammalian nitric oxide synthases", Biochimica et Biophysica Acta, 1411, (1999), 217-230.
Wayne, L. G., et al., "An In Vitro Model for Sequential Study of Shiftdown of *Mycobacterium tuberculosis* through Two Stages of Nonreplicating Persistence", Infection and Immunity, 64(6), (1996), 2062-2069.
Wayne, L. G., et al., "Nitrate reduction as a marker for hypoxic shiftdown of *Mycobacterium tuberculosis*", Tubercle and Lung Disease, 79(2), (1998), 127-132.
Wilkinson, D., et al., "Diagnosing tuberculosis in a resource-poor setting: the value of sputum concerntration", Transactions of the Royal Society of Tropical Medicine and Hygiene, 91(4), (1997), 420-421.

* cited by examiner

Primary Examiner — Allison Ford
Assistant Examiner — Michelle F Paguio Frising
(74) Attorney, Agent, or Firm — Schwegman, Lundberg & Woessner, P.A.

(57) ABSTRACT

The present invention discloses functional nitrite reductase as a potential drug target for anti-tubercular drug development. The present invention also relates to the development of an easy method for identification of nitrite in clinical samples as well as its correlation with the severity of the disease. Presence of active as well as dormant/latent stages of *Mycobacterium tuberculosis* (MTB) could be identified from nitrite in clinical samples like sputum of potential TB patients.

6 Claims, 4 Drawing Sheets

SEQUENCE LISTING

<160> NUMBER OF SEQ ID NOS: 10

<210> SEQ ID NO 1
<211> LENGTH: 30
<212> TYPE: DNA
<213> ORGANISM: ARTIFICIAL SEQUENCE
<220> FEATURE:
<223> OTHER INFORMATION: narG : Forward primer

<400> SEQUENCE: 1
actacgccga caacaccaag ttcgccgacg                30

<210> SEQ ID NO 2
<211> LENGTH: 30
<212> TYPE: DNA
<213> ORGANISM: ARTIFICIAL SEQUENCE

```
<220> FEATURE:
<223> OTHER INFORMATION: narG :Reverse primer

<400> SEQUENCE: 2
agcggcgcac atagtcgaca aagaacggaa                                30

<210> SEQ ID NO 3
<211> LENGTH: 20
<212> TYPE: DNA
<213> ORGANISM: ARTIFICIAL SEQUENCE
<220> FEATURE:
<223> OTHER INFORMATION: nirB : Forward primer

<400> SEQUENCE: 3
gtcccggttc gtttccttcg                                           20

<210> SEQ ID NO 4
<211> LENGTH: 20
<212> TYPE: DNA
<213> ORGANISM: ARTIFICIAL SEQUENCE
<220> FEATURE:
<223> OTHER INFORMATION: nirB : Reverse primer

<400> SEQUENCE: 4
cgcgggatac caatggacac                                           20

<210> SEQ ID NO 5
<211> LENGTH: 24
<212> TYPE: DNA
<213> ORGANISM: ARTIFICIAL SEQUENCE
<220> FEATURE:
<223> OTHER INFORMATION: glnA : Forward primer

<400> SEQUENCE: 5
caacttcttt gtgcacgacc cgtt                                      24

<210> SEQ ID NO 6
<211> LENGTH: 24
<212> TYPE: DNA
<213> ORGANISM: ARTIFICIAL SEQUENCE
<220> FEATURE:
<223> OTHER INFORMATION: glnA : Reverse primer

<400> SEQUENCE: 6
aactggtagt tgatctcggc ctgt                                      24

<210> SEQ ID NO 7
<211> LENGTH: 30
<212> TYPE: DNA
<213> ORGANISM: ARTIFICIAL SEQUENCE
<220> FEATURE:
<223> OTHER INFORMATION: narK2 : Forward Primer

<400> SEQUENCE: 7
tgcttcgtga tgcaccctac tttcggccca                                30

<210> SEQ ID NO 8
<211> LENGTH: 30
<212> TYPE: DNA
<213> ORGANISM: ARTIFICIAL SEQUENCE
<220> FEATURE:
<223> OTHER INFORMATION: nark2 : Reverse Primer

<400> SEQUENCE: 8
ccgccgaaca cgatcgcgta cagaaacgac                                30
```

-continued

```
<210> SEQ ID NO 9
<211> LENGTH: 24
<212> TYPE: DNA
<213> ORGANISM: ARTIFICIAL SEQUENCE
<220> FEATURE:
<223> OTHER INFORMATION: 16S : Forward primer

<400> SEQUENCE: 9
atgcatgtct tgtggtggaa agcg                                            24

<210> SEQ ID NO 10
<211> LENGTH: 24
<212> TYPE: DNA
<213> ORGANISM: ARTIFICIAL SEQUENCE
<220> FEATURE:
<223> OTHER INFORMATION: 16S : Reverse primer

<400> SEQUENCE: 10
ttcacgaaca acgcgacaaa ccac                                            24
```

NITRITE-REDUCTASE (NIRB) AS POTENTIAL ANTI-TUBERCULAR TARGET AND A METHOD TO DETECT THE SEVERITY OF TUBERCULOSIS DISEASE

TECHNICAL FIELD OF INVENTION

The present invention relates to nitrite reductase as an anti-tubercular drug target. The present invention also relates to the development of an easy method for identification of nitrite in clinical samples as well as its correlation with the severity of the disease. Presence of active as well as dormant/latent stages of *Mycobacterium tuberculosis* (MTB) could be identified from nitrite in clinical samples like sputum of potential tuberculosis (TB) patients.

BACKGROUND OF THE INVENTION

Tuberculosis (TB) is responsible for causing 5 million deaths annually. The presence of increased number of people having double infections with MTB and human immunodeficiency virus emphasizes the importance of controlling this infection. The major problem in treating the disease lies in the fact that most of the infections are asymptomatic and latent. About 3 billion world population is infected with latent form of TB which if left untreated, kills more than 50% of the infected people. Further, the treatment of TB requires administration of multiple antibiotics over a long period of time. This leads to development of multiple drug-resistant tuberculosis (MDR-TB) infection aggravating the problems of TB treatment.

The World Health Organization has therefore declared as a priority the need to immediately control tuberculosis infection to prevent the spread of drug-resistant strains.

Infection of a mammalian host by *M. tuberculosis* usually occurs by the aerosol route, and the macrophages in the lung are typically affected. Macrophages are among the most important players in the characteristic immune defenses that control different infectious processes. Non-replicating *M. tuberculosis* bacilli under in vitro culture conditions are characteristically resistant to most of the anti-tubercular agents and usually known as dormant bacilli. It is documented that non-pulmonary tissue oxygen concentrations within the human body are well below the oxygen concentration in ambient room air. Furthermore, the oxygen concentration in the phagosome of activated macrophages is lower than the extracellular oxygen concentration. The MTB cells within lipid-loaded macrophages lose acid-fast staining, becoming phenotypically resistant to the two frontline anti-mycobacterial drugs rifampicin and isoniazid, and induce gene transcripts involved in dormancy and lipid metabolism within the pathogen. The pathogen thus acquires the phenotypically drug-resistant non-replicating state during latent infection and creates major hindrance to curing the disease. Hence, humans harboring latent tuberculosis infection (LTBI) carry a lifetime risk of reactivation to active disease.

Early detection of TB is therefore of paramount importance in curing this fatal infection. A definitive diagnosis of tuberculosis can only be made by culturing *Mycobacterium tuberculosis* organisms from a specimen taken from the patient (most often sputum, but may also include pus, CSF, biopsied tissue, etc. (Virtanen S. (1960). *Acta Tuberc. Scand.* 47: 1-116). A diagnosis made other than by culture may only be classified as "probable" or "presumed". For a diagnosis negating the possibility of tuberculosis infection, most protocols require that two separate cultures both test negative (Virtanen S. (1960). *Acta Tuberc. Scand.* 47: 1-116). A complete medical evaluation for TB must include a medical history, a physical examination, a chest X-ray and microbiological examination (of sputum or some other appropriate sample). It may also include a tuberculin skin test, other scans and X-rays, surgical biopsy. A physical examination is done to assess the patient's general health and find other factors which may affect the TB treatment plan. It cannot be used to confirm or rule out TB. Certain cases require a specimen that cannot be supplied by sputum culture or bronchoscopy. In these cases, a biopsy of tissue from the suspected system can be obtained by mediastinoscopy.

Interferon-γ (interferon-gamma) release assays (IGRAs) are based on the ability of the *Mycobacterium tuberculosis* antigens for early secretary antigen target 6 (ESAT-6) and culture filtrate protein 10 (CFP-10) to stimulate host production of interferon-gamma. Because these antigens are not present in non-tuberculous mycobacteria or in BCG vaccine, these tests can distinguish latent tuberculosis infection (LTBI). The blood tests QuantiFERON-TB Gold and T-SPOT.TB use these antigens to detect people with tuberculosis. Lymphocytes from the patient's blood are cultured with the antigens. These tests are called interferon γ tests and are not equivalent. If the patient has been exposed to tuberculosis before, T lymphocytes produce interferon γ in response. Both tests use ELISA to detect the interferon γ with great sensitivity. The distinction between the tests is that QuantiFERON-TB Gold quantifies the total amount of interferon γ when whole blood is exposed to the antigens, whereas T-SPOT.TB, a type of ELISPOT assay, counts the number of activated T lymphocytes that secrete interferon γ. Guidelines for the use of the FDA approved QuantiFERON-TB Gold were released by the CDC in December 2005. The overall purpose of the present invention is to find a diagnostic tool to assess the presence of dormant tubercle bacilli in humans. Our diagnostic procedure mainly relies on the sensitivity towards tubercular metabolite. Major problem of current tuberculosis treatment lies also in its inability to assess the conversion of active to dormant bacilli in humans Drug induced dormant bacilli is not killed by currently available drugs and is also the major reason for resistance and long treatment period.

There is no diagnostic method available to check the increase or decrease of bacilli after the treatment has started. Available techniques rely on either immunological or staining technique or culturing of actively growing bacilli. These methods work particularly at a very initial stage when the patient is critically ill and has not just started taking medicine. It becomes ineffective within few weeks of starting the treatment. Major problem lies in the failure to detect the bacilli present in dormant stage and not effectively killed by medicine. In most of the hospitals, the methods followed on a regular basis do not detect the bacilli with surety. As a result, patients are compelled to follow wrong diagnosis.

Moreover, identification of the intracellular target of a lead inhibitor is imperative for pursuing the requisite lead program.

Wayne's hypoxia and nutrient starvation-induced dormancy models were developed to explain certain features in persistent tubercular bacilli obtained from hosts. Pioneering work by Wayne showed that nitrate reductase (NarGHJI) played an important role during transition from the aerobic to anaerobic dormant stage and that this transition occurs during initial exposure to the asymptomatic pathogenesis as well as during exposure to anti-tubercular medicines.

Recent reports suggest that nitric oxide (NO) and superoxide ($O_2^-$) are generated inside host macrophages and kill the intracellular bacilli after infection by combining to form highly unstable peroxynitrite ($ONOO^-$), which subsequently rearranges to produce $NO_3^-$ (Nyka, W. studies on the effect of starvation on Mycobacteria. Infect. Immun. 1973, 843-850) that can act as a source of nitrogen or as an alternate electron acceptor during hypoxia-induced dormancy in absence of oxygen. These findings indicate that nitrate metabolic pathway plays a crucial role in *Mycobacterium tuberculosis* survival under dormancy.

Article titled "Nitrate reduction as a marker for hypoxic shiftdown of *Mycobacterium tuberculosis*" by L. G. Wayne, L. G. Hayes in Journal: Tubercle and Lung Disease—TUBERCLE LUNG DIS", Vol. 79, no. 2, pp. 127-132, 1998, DOI: 10.1054/tuld.1998.0015 characterizes nitrate reduction during aerobic growth and hypoxic shift down to non-replicating persistence of *Mycobacterium tuberculosis* cultures.

Article titled "Bactericidal activity of 2-nitroimidazole against the active replicating stage of *Mycobacterium bovis* BCG and *Mycobacterium tuberculosis* with intracellular efficacy in THP-1 macrophages" by Arshad Khan, Sampa Sarkar, Dhiman Sarkar in International Journal of Antimicrobial Agents, Volume 32, Issue 1, July 2008, Pages 40-45 evaluates the anti-tubercularous potential of 2-nitroimidazole, under in vitro conditions, against *M. tuberculosis* in the intracellular environment of the human monocytic cell line THP-1.

Moreover, Glutamine synthetase (GS), another enzyme in nitrate metabolic pathway is known to convert ammonia and glutamate to glutamine, which is the only known pathway for ammonia utilization in MTB and is observed to be essential for the synthesis of poly L-glutamate/glutamine in cell wall formation.

$$NADH + H^+ \quad NAD^+ + H_2O$$

[Scheme showing nitrate metabolic pathway: $NO_3^-$ converted to $NO_2^-$ by NR, then to $HNO_2$ with $H^+$, to $HNO_2$, to $NH_3$ via Nii with 6 e⁻, then $NH_3$ combines with glutamate + ATP, and via GOGAT with 2-oxoglutarate and 2e⁻ produces glutamine and glutamate]

Scheme 1: Nitrate Metabolic Pathway in Bacterial System. NR—Nitrate Reductase, Nir—Nitrite Reductase and GS—Glutamine Synthetase Nitrate reduction is found to be induced during transition of actively growing cells into hypoxic condition. Nitrate is used as alternate respiratory substrate for accepting electrons in absence of $O_2$ in the medium; however, no physiological investigation has been carried out on nitrite reductase that provides a metabolic link between nitrate reductase (NarGHJI) and glutamine synthetase (GS) which can help in understanding the role of nitrate metabolism during dormancy. So far, GS is reported to play an essential role in growing aerobic bacilli. Its role in dormant bacilli is unknown. Host macrophages are reported to produce NO and superoxide to kill intracellular bacilli, which is supposed to combine and rearrange to produce nitrate inside infected macrophages. Unless hypoxia is achieved, this nitrate is not required either as respiratory substrate or as nitrogen source for survival within host environment. In fact, the functional role of nitrate metabolic pathway of *Mycobacterium tuberculosis* during survival within host macrophages has remained unexplored so far. The reported estimates of net nitrate synthesis by mammalian tissue vary greatly and range from 0.15 to 1 mM day −1 (Kelm M. (1999) *Biochim. Biophys. Acta* 1411: 273-289). Within the tissue, nitrate is mainly a product of spontaneous degradation of nitric oxide. Nitric oxide, in contrast, is produced enzymatically by three different nitric oxide synthetases (Stuehr D J. 1999. *Biochim. Biophys. Acta* 1411: 217-230). An inducible nitric oxide synthetase is expressed in response to inflammatory and proinflammatory mediators (Bogdan C, et. al. (2000) *Curr. Opin. Immunol.* 12: 64-76). A variety of cells, including hepatocytes, can be induced to synthesize nitric oxide (Brown G C. (1999) *Biochim. Biophys. Acta* 1411:351-369). Significant amounts of nitrate are detected in the urine of mice infected with bacteria, suggesting that nitrate is available in the kidney, especially in animals undergoing an inflammatory process (Flesch I E, et. A1/(1991) *Infect. Immun.* 59: 3213-3218). Although nitrite in urine samples is being used for the detection of UTI infection, there is no report of using either nitrate or nitrite in the detection of TB.

The latent tubercle bacilli are broadly suggested to be present in granulomas structures within infected humans. Surprisingly, Cornell model of drug induced dormancy suggests exposure of bacilli within animal host induces latency and these cells reactivate to the actively growing stage as soon as the drugs are withdrawn. It is well known that in presence of even trace amount of nitrate/nitrite, survival of bacilli becomes dependent on their use as alternate electron acceptor under hypoxic conditions. But the question still remains in the aspect of *Mycobacterium tuberculosis* survival during its transition from actively growing to dormant stage with the help of this very weak supply of nitrate at an inaccessible place within our body. At this stage it is unexpected that detection of *Mycobacterium tuberculosis* cells would be possible from still lower conversion of this low level of nitrate in body fluids. The question also arises as to how these latent bacilli are reactivated so easily but not the latent bacilli residing within our body under normal conditions. Apart from addressing the problem associated with latency of the bacilli as well as the failure of current screening methods in identifying latent stage specific anti-mycobacterial drugs is a pressing need to provide a drug target which could additionally function as biomarker for the identification of active and dormant stage inhibitors of *Mycobacterium tuberculosis*.

SUMMARY OF THE INVENTION

Accordingly the present invention provides nitrate metabolic pathway enzymes including nitrate reductase (narG), nitrite reductase (MRA_0261) and glutamine synthetase (glnA1) as drug target proteins against the dormant stage of *Mycobacterium tuberculosis* (MTB) under aerobic, hypoxia induced dormancy and in Human acute monocyte leukemia cell line Thp1 macrophages.

In another aspect, the present invention provides nitrate metabolic pathway enzyme particularly functional nitrite reductase as a potential drug target against the dormant stage of *Mycobacterium tuberculosis* under aerobic, hypoxia induced dormancy and in Human acute monocyte leukemia cell line Thp1 macrophages for anti-tubercular drug development.

In a preferred aspect, the present invention provides a method for detection of nitrite in body fluids of TB patients as a potential diagnostic tool for diagnosis of various stages of tuberculosis infection in humans.

DETAILED DESCRIPTION OF THE INVENTION

Figure 1A:
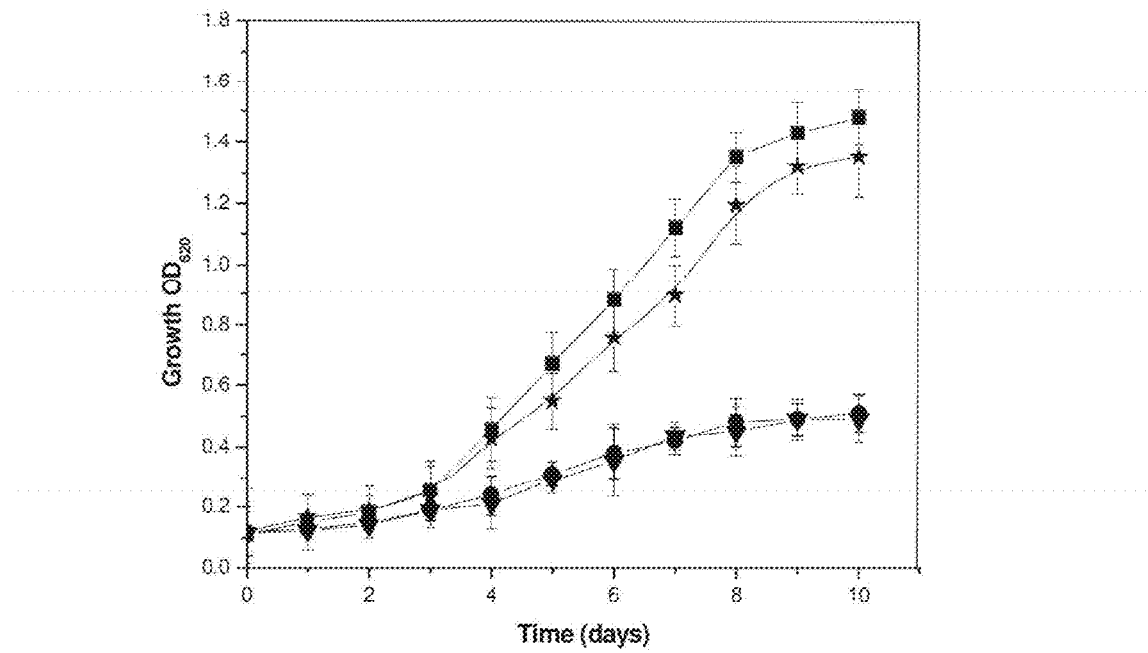
FIG. 1 shows the growth of M. tuberculosis and its nitrate/nitrite reduction in aerobic and Wayne dormancy culture. (a) Growth under aerobic (Filled line) and Wayne model (open line) in minimal medium in presence of nitrate and nitrite as sole nitrogen source. (b) Nitrite reduction under aerobic (-★-) and Wayne model culture (-▽-) were measured under identical conditions as described in "Materials and methods". Growth of bacilli in presence of nitrate and its reduction under aerobic (-★-) and Wayne model culture) (-▽-) taken as positive control. The growth of M. tuberculosis in presence of nitrate under aerobic condition (—■—) and Wayne model culture (—□—) is used as positive control in Fig (a). The utilization of nitrate under identical conditions in aerobic culture (—●—) and Wayne model (—○—) is shown in Fig (b). The results were an average reading of three identical experiments with ±S.D.
Figure 1B:
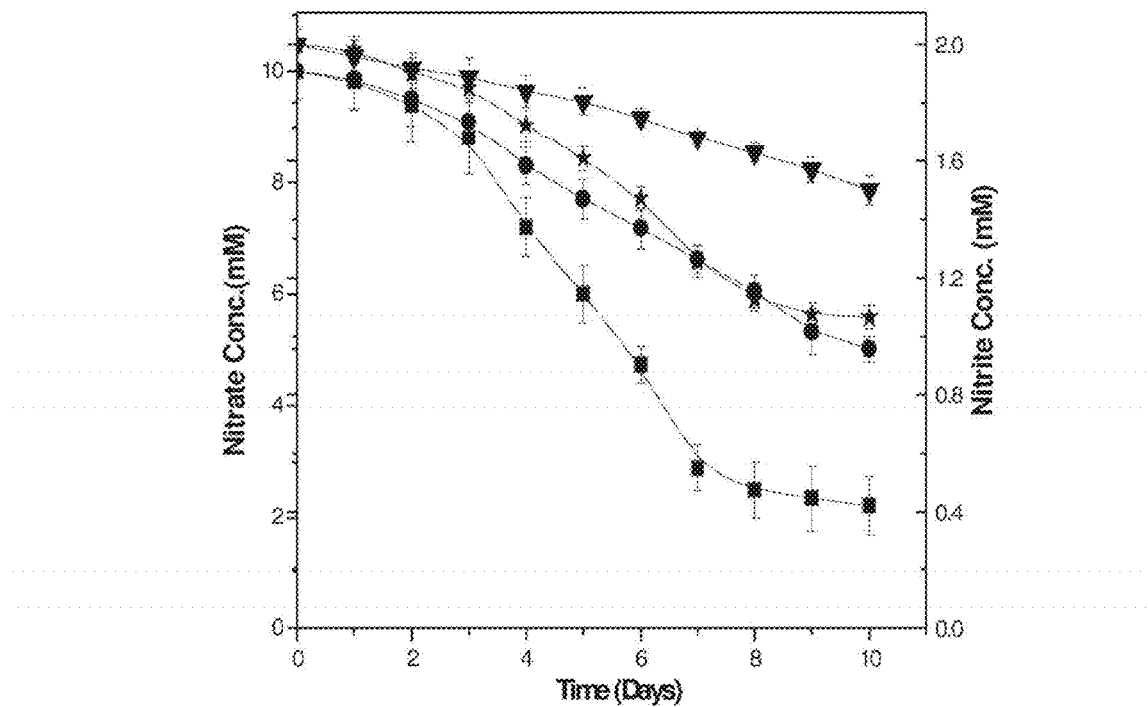

The invention will now be described in detail in connection with certain preferred and optional embodiments, so that various aspects thereof may be more fully understood and appreciated. The embodiments as described are not limiting or restricting the scope of the invention.

Mycobacterium tuberculosis (MTB) can utilize nitrate as a nitrogen source during its growth under in vitro and in vivo conditions. The nitrate is reduced to nitrite which is further converted into ammonia by nitrate reductase and nitrite reductase enzymes respectively. Nitrate reductase (NarGHJI) is well characterized enzyme and its role as part of alternate respiratory mechanism in MTB under in vitro conditions is established, but its similar role in macrophage is completely unknown. Similarly, the role of nitrite reductase (NirBD) under hypoxia induced dormancy (Wayne model) and THP-1 macrophage is however not known hitherto, for Mycobacterium tuberculosis. The present inventor has therefore explored the use of nitrite reductase, which is a metabolic link between nitrate reductase (NarGHJI) and glutamine synthetase (GS) which can help in understanding the role of nitrite metabolism during dormancy and which can be used as a potential drug target or a biomarker to develop antitubercular screening protocol.

The inventors acknowledge that a possible gene encoded by nitrite reductase enzyme (EC: 1.7.1.4) is present in the genome of Mycobacterium tuberculosis, which consists of two subunits nirB (MRA_0261) and nirD (MRA_0262). This nitrite reductase is NADH dependent which acts as a source of six electrons required for reduction of nitrite into ammonia similar to reported E. coli cytoplasmic nitrite reductase (NirBD).

Nitrite reductase (NirBD) is an important functional enzyme of nitrogen metabolic pathway that converts nitrite to ammonia. In spite of the presence of a function nitrite reductase enzyme, the release of nitrite in the medium is a mystery. It is been suggested the nitrite so formed is released to extracellular medium due to non-functional nitrite reductase to overcome the possible toxic effect of nitrite. If nitrite reductase is truly non-functional then the amount of nitrate utilized should balance the nitrite release in the medium. In order to become a drug target, apart from essentiality, the protein needs to fulfill certain other criteria. Our studies have clearly shown that inhibitor of the enzyme has effect on bacilli viability during hypoxia only as well as within macrophages. This is the most important aspect in deciding nirB as drug target because after drugs are also inhibitors and they have to work in complex body fluids where all the other nitrogen sources will be available in plenty. Increased conversion of nitrate to nitrite within hypoxia induced dormant stage also induces the expression of nitrite reductase in *Mycobacterium tuberculosis* under in vitro conditions which implicates its importance during this transition to non-replicating dormancy suggesting it to be a potential anti-tubercular drug target.

Thus, in an embodiment, the present invention relates to nitrite reductase as a potential drug target against the active and dormant stage of *Mycobacterium tuberculosis* (MTB) under aerobic, hypoxia induced dormancy and in Human acute monocyte leukemia cell line Thp1 macrophages.

In an embodiment of the present invention, there is provided a method for screening inhibitors against nitrite reductase useful as anti tubercular drug comprising: infecting Thp1 macrophage culture with *M. tuberculosis*; washing the infected macrophage culture with 1×PBS solution followed by adding fresh medium (MEM) containing 50 mM of sodium nitrate; adding 2.5 µl of inhibitors in DMSO along with the standard inhibitors of narG, nirB and glnA1 at their respective IC90 to the infected macrophage culture on 0 d and 5 d respectively and incubating the plate for 8 d; and estimating the level of ammonia/nitrite in the culture medium for determining the viable cell count.

In another embodiment of the present invention, there is provided a method for screening inhibitors against nitrite reductase useful as anti tubercular drug comprising: infecting Thp1 macrophage culture with *M. tuberculosis*; washing the infected macrophage culture with 1×PBS solution followed by adding fresh medium (MEM) containing 50 mM of sodium nitrate; adding 2.5 µl of inhibitors in DMSO along with the standard inhibitors of narG, nirB and glnA1 at their respective IC90 to the infected macrophage culture on 0 d and 5 d respectively and incubating the plate for 8 d; and estimating the level of ammonia/nitrite in the culture medium for determining the viable cell count, wherein the inhibitors are selected from the group comprising of enzymes belonging to nitrate metabolic pathway that kill dormant/latent *Mycobacterium tuberculosis* bacilli.

Another embodiment of the present invention provides a method for screening inhibitors against nitrite reductase useful as anti tubercular drug comprising: infecting Thp1 macrophage culture with *M. tuberculosis*; washing the infected macrophage culture with 1×PBS solution followed by adding fresh medium (MEM) containing 50 mM of sodium nitrate; adding 2.5 µl of inhibitors in DMSO along with the standard inhibitors of narG, nirB and glnA1 at their respective IC90 to the infected macrophage culture on 0 d and 5 d respectively and incubating the plate for 8 d; and estimating the level of ammonia/nitrite in the culture medium for determining the viable cell count, wherein the inhibitors are selected from the group comprising of rifampicin, pentachlorophenol, streptomycin, isoniazid, ethambutol, pyrazinamide.

In yet another embodiment of the present invention, there is provided a method for screening inhibitors against nitrite reductase useful as anti tubercular drug comprising: infecting Thp1 macrophage culture with *M. tuberculosis*; washing the infected macrophage culture with 1×PBS solution followed by adding fresh medium (MEM) containing 50 mM of sodium nitrate; adding 2.5 µl of inhibitors in DMSO along with the standard inhibitors of narG, nirB and glnA1 at their respective IC90 to the infected macrophage culture on 0 d and 5 d respectively and incubating the plate for 8 d; and estimating the level of ammonia/nitrite in the culture medium for determining the viable cell count, wherein the inhibitors are against active and dormant stage of *Mycobacterium tuberculosis* (MTB).

In still another embodiment of the present invention, there is provided a method for screening inhibitors against nitrite reductase useful as anti tubercular drug comprising: infecting Thp1 macrophage culture with *M. tuberculosis*; washing the infected macrophage culture with 1×PBS solution followed by adding fresh medium (MEM) containing 50 mM of sodium nitrate; adding 2.5 µl of inhibitors in DMSO along with the standard inhibitors of narG, nirB and glnA1 at their respective IC90 to the infected macrophage culture on 0 d and 5 d respectively and incubating the plate for 8 d; and estimating the level of ammonia/nitrite in the culture medium for determining the viable cell count, wherein the bacilli is under aerobic, hypoxia induced dormancy and in Human acute monocyte leukemia cell line Thp1 macrophages.

An embodiment of the present invention provides use of inhibitors against nitrite reductase as a drug target against *Mycobacterium tuberculosis* (MTB) in a method for screening inhibitors against nitrite reductase useful as anti tubercular drug comprising: infecting Thp1 macrophage culture with *M. tuberculosis*; washing the infected macrophage culture with 1×PBS solution followed by adding fresh medium (MEM) containing 50 mM of sodium nitrate; adding 2.5 µl of inhibitors in DMSO along with the standard inhibitors of narG, nirB and glnA1 at their respective IC90 to the infected macrophage culture on 0 d and 5 d respectively and incubating the plate for 8 d; and estimating the level of ammonia/nitrite in the culture medium for determining the viable cell count.

In an embodiment of the present invention there is provided a method for detecting the severity of tuberculosis in humans comprising: providing body fluid from the subject; adding reagents A and B to the sample obtained in the first step; detecting color intensity of the solution obtained in the second step, where magenta as indicator of most severity with respect to the disease and faintly pink is less; and detecting the titre of bacilli present in the sample obtained in the second step, where in the color level is determined by comparing with color coded strips or standard color codes.

In yet another embodiment of the present invention, there is provided a method for detecting the severity of tuberculosis in humans comprising: providing body fluid from the subject; adding reagents A and B to the sample obtained in the first step; detecting color intensity of the solution obtained in the second step, where magenta as indicator of most severity with respect to the disease and faintly pink is less; and detecting the titre of bacilli present in the sample obtained in the second step, where in the color level is determined by comparing with color coded strips or standard color codes, wherein the bacilli is detected in the clinical sample comprising body fluids selected from the group consisting of sputum, urine, blood, etc.

In still another embodiment of the present invention, there is provided a method for detecting the severity of tuberculosis in humans comprising: providing body fluid from the subject; adding reagents A and B to the sample obtained in the first step; detecting color intensity of the solution obtained in the second step, where magenta as indicator of most severity with respect to the disease and faintly pink is less; and detecting the titre of bacilli present in the sample obtained in the second step, where in the color level is determined by comparing with color coded strips or standard color codes, wherein the reagent A is sulphanilic acid.

Another embodiment of the present invention, there is provided a method for detecting the severity of tuberculosis in humans comprising: providing body fluid from the subject; adding reagents A and B to the sample obtained in the first step; detecting color intensity of the solution obtained in the second step, where magenta as indicator of most severity with respect to the disease and faintly pink is less; and detecting the titre of bacilli present in the sample obtained in the second step, where in the color level is determined by comparing with color coded strips or standard color codes, wherein the reagent B is NEDD.

In an embodiment of the present invention, there is provided a diagnostic kit for the detection of *Mycobacterium tuberculosis* (M. tb or M. Tb or MTB) disease, comprising of reagents sulphanilic acid and NEDD, along with an instructions manual and optionally along with additives and carriers.

Another embodiment of the present invention provides use of a diagnostic kit for the detection of *Mycobacterium tuberculosis* disease, comprising of reagents sulphanilic acid and NEDD, along with an instructions manual and optionally along with additives and carriers, for detecting the severity of the *Mycobacterium tuberculosis* disease.

To characterize nitrite reductase (NirBD), nirB gene studies are carried out in *Mycobacterium tuberculosis* grown under different conditions. *Mycobacterium tuberculosis* reduces nitrite during aerobic and dormant conditions due to presence of functional nirB genes. The nitrite reductase expression increases at transcript and protein levels by 32 and 4-fold respectively during in vitro hypoxia induced dormancy condition while 10-fold increase in gene expression is observed in macrophages infection as compared to the aerobic conditions.

Figures 2, 3:
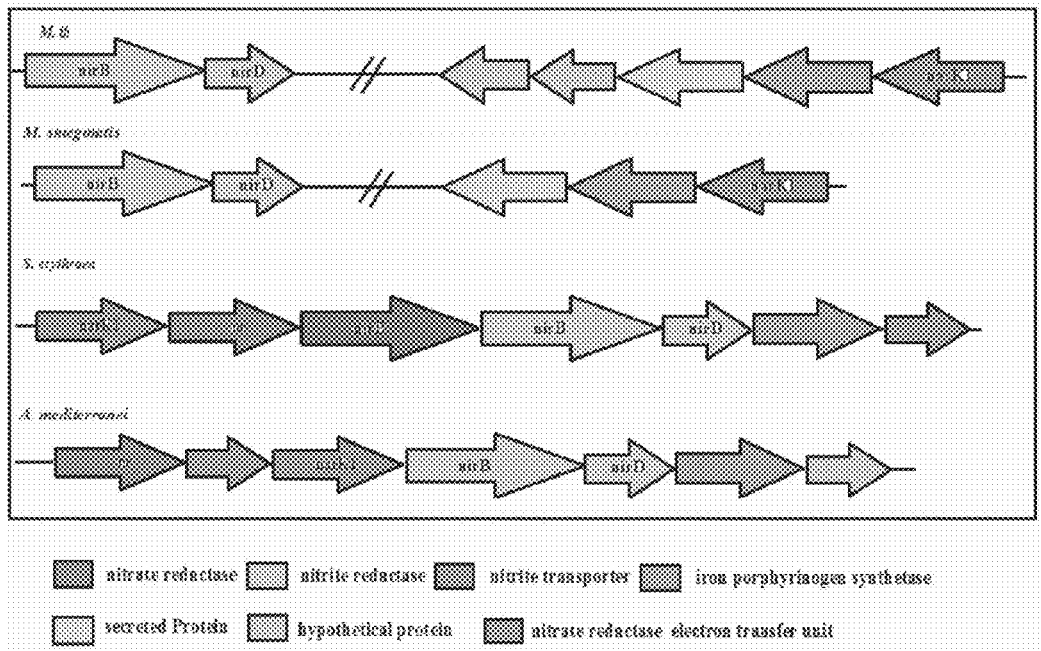
FIG. 2 shows different localization of genes in nirB operon system of organisms from actinomycetis group. The nitrite reductase operon of M. tuberculosis and M. smegmatis (ID 336089/ID 260240) was analyzed by using DOOR operon analysis software (csbl1.bmb.uga.edu/OperonDB/) to generate an overview of the localization of different metabolic genes in a specific operon. nirB and nirD, the larger and smaller subunit of functional nitrite reductase enzyme are localized in the same operon system in both M. tuberculosis and M. smegmatis. Further gene sequence of nirB and nirD reveals that stop codon of nirB overlaps the start codon of nirD subunit which indicates that both the subunits are synthesized as single transcript, but this operon does not consist of any transporter gene which can carry nitrite ions across the cell membrane.
FIG. 3 shows the expression of Mycobacterium tuberculosis genes involved in nitrate metabolism under aerobic and Wayne model condition in presence of different nitrogen sources. cDNA was prepared from total RNA isolated from bacilli grown in presence of nitrate/nitrite/ammonia/asparagine separately under both aerobic ($+O_2$) and anaerobic ($-O_2$) conditions as described in "Materials and Methods". cDNA was used as templates for PCR amplification using gene specific primers for narG (nitrate reductase), nirB (nitrite reductase) and glnA1 (glutamine synthetase) and the amplified products are shown after electrophoresis on agarose gel. Lane (−): shows negative control where cDNA was not added, while M represents 100 bp Marker (Invitogen).

To confirm nitrite reductase gene expression at the transcript level, RT-PCR is performed using cDNA synthesized from total RNA isolated from bacilli grown in different nitrogen sources (FIG. 3). The RT-PCR result shows nitrate reductase MRA_1172 (narG), nitrite reductase MRA_261 (nirB), and glutamine synthetase MRA_2230 (glnA1) genes are expressed when nitrate was used as a sole nitrogen source while nitrite reductase MRA_261 (nirB) and glutamine synthetase MRA_2230 (glnA1) genes are induced specifically in presence of nitrite as a source of nitrogen.

The culture selected for the purpose of the invention is *Mycobacterium tuberculosis* (ATCC 25177), obtained from the Microbial Type Culture Collection (MTCC; Chandigarh, India). *Mycobacterium tuberculosis* can grow in nitrate as sole nitrogen source both under aerobic and anaerobic conditions which is reduced to nitrite by functional nitrate reductase. Accordingly, the present invention discloses a time-dependent study of nitrite utilization under aerobic and anaerobic conditions by *Mycobacterium tuberculosis* grown with nitrate as sole nitrogen source (10 mM) as shown in Table 1.

In an embodiment, the present invention provides inhibitors of enzyme belonging to nitrate metabolic pathway that kills dormant/latent *Mycobacterium tuberculosis* bacilli.

THP-1 cell line (ATCC® Cat. no. TIB-202™) is maintained in a 25 $cm^2$ tissue culture flask containing MEM (minimum essential medium) cell culture medium with 10% heat-inactivated FBS. The THP-1 cell ($5 \times 10^4$ cells/ml) is treated with 100 nM phorbol myristate acetate in a culture flask for 24 h to convert monocytes to macrophages. These macrophage cells are incubated for 12 h with M.Tb at multiplicity of infection (MOI) of 1:100 for infection.

In an embodiment, the present invention provides nirB inhibitor p-hydroxy mercuric benzoate as nirB inhibitor and effect of nirB inhibitor in *Mycobacterium tuberculosis* survival within host macrophages cells during infection. Application of nirB inhibitor reduces the bacilli count by ~2 log cfu value in an in-vitro and ex-vivo conditions, clearly establishing an important role of nitrite reductase in the survival of bacilli under different environments.

In yet another embodiment, the present invention provides cytotoxicity assessment of Inhibitor on THP-1 macrophages cell line.

In another embodiment, the invention provides Fluorescence Microscopic study of THP-1 in presence of inhibitor.

In an embodiment, the present invention provides inhibitors of the enzymes belonging to nitrate metabolic pathway could effectively kill the dormant/latent *Mycobacterium tuberculosis* bacilli within the host system. The inhibitors of nitrate reductase, nitrite reductase and glutamine synthetase also affected bacilli viability under hypoxia induced dormant culture conditions in presence of their respective metabolites in the medium. The pattern of inhibition clearly indicates that these inhibitors exert their inhibitory action very similarly on the hypoxic cultures of *Mycobacterium tuberculosis* cells. The pattern of inhibition on intracellular bacilli also is very similar when macrophages are loaded with bacilli In yet another embodiment, the present invention relates to a method for detection of nitrite in clinical samples obtained from TB patients like sputum sample as a potential tool for the diagnosis of tuberculosis in humans.

In another embodiment, the present invention relates the use of body fluids for the detection of nitrite in clinical sample to correlate with the severity of the disease. The reagents A and B are used to develop color proportional to nitrite present in clinical samples. The intensity of color developed due to the addition of reagents A and B is proportional to the bacilli burden in the patients. With the increase in concentration of nitrite in the sample, the color is found to develop from pinkish to pink to purple to magenta. The sputum samples collected from patients died because of the failure in identifying TB in some patients by currently used methods of a) microscopic detection of acid fast bacilli and b) X-Ray analysis of chest. The whole experiment was carried out at Aundh TB Hospital, Pune as well as Medipoint Hospital, Pune. So, we could accordingly identify magenta as indicator of most severity with respect to the disease and faintly pink is least.

In another embodiment, the present invention discloses that nitrite estimation procedure is a far better method than at least chest X-Ray and Acid Fast Bacilli microscopy because nitrite estimation method is able to identify double number of patients having TB than the X-Ray and Acid Fast Bacilli microscopic detection jointly done. Some of the samples developed purple/magenta color by nitrite reagents (A & B) were surprisingly identified as negative in microscopic method as a result the patients expired within few days.

In yet another embodiment, the present invention discloses that nitrite is equally sensitive for drug resistant bacilli.

In another embodiment, the present invention discloses that this nitrite detection in sputum sample is very robust and easy to perform without having any sophisticated instrument in the laboratory. Sputum is a heterogeneous mass from which only relatively solid portion should be taken for microscopic study whereas nitrite reagent could be applied on any part of the sputum as well as whole content for testing purpose. The color develops within 30 seconds and stable for hours.

In another embodiment, the present invention discloses that this nitrite detection in sputum sample does not require any expertise in carrying out this test whereas other procedures require significant expertise in respective field of applications. The reagents (A & B) are cheap chemicals and easily available everywhere.

In another embodiment, the present invention discloses that samples collected in the morning shows more color in nitrite detection than samples collected in the evening.

Accordingly, the present invention provides a rapid, easy and cost saving method for detection of nitrite in sputum of TB patients as a potential diagnosis of tuberculosis in humans. The assay has the following advantages:
 i) The assay requires addition of reagent A and B to the clinical samples which are easily available at minimum cost.
 ii) The addition of reagents as well as detection of color does not require any sophisticated instruments.
 iii) The intensity of color represents the level of *Mycobacterium tuberculosis* infection within the patients.
 iv) Drug resistant patients are observed to be equally responsive to the detection/diagnostic reagents.
 v) The color development happens very fast and easily discriminative thus can be used in remote areas where facilities are not available.
 vi) Other reagents like sulfuric acid and ferrous sulfate can also be used to detect nitrite in clinical samples
 vii) The method is very robust and detects TB in double number of samples that jointly detected by chest X-ray as well as microscopy of Acid Fast Bacilli. Most of the false positive and negatives were also detected by our nitrite detection method.
 viii) Nitrite could also be detected by using sensitive/specific electrodes or strips available in the market for nitrite detection in liquid samples
 ix) Morning samples provide better results than the samples collected in the evening.

Thus, human clinical samples like sputum samples could be useful for this detection of MTB in humans. Some of the false positives in microscopic technique can also be identified by the current method.

The present invention demonstrates that nitrite supports the growth of *Mycobacterium tuberculosis* within in vitro culture and nirB gene (which is responsible for nitrite reduction) expression can be induced in presence of nitrate or nitrite as sole nitrogen source under aerobic and anaerobic conditions. Furthermore, the increased nirB gene expression during hypoxia induced dormant culture and in macrophages infection along with decrease survival of bacilli in presence of NirBD inhibitor shows an important role of nitrite reductase in bacterial survival. The nitrite reductase inhibitor like p-HMB is able to kill dormant bacilli under in vitro hypoxic culture condition as well as within macrophages. Further, nitrite reductase gene is up-regulated under hypoxic conditions in presence of nitrate and nitrite in the medium as well as within infected macrophages. Nitrite reductase is however not up-regulated if medium is supplemented with other nitrogen sources whereas extraneous addition of nitrite in culture is not required to induce nitrite reductase in intracellular bacilli within infected macrophages.

EXAMPLES

The following examples are given by way of illustrations and should not be construed to limit the scope of the present invention.

Example 1 a. Reagents

Sulphanilic acid, N-(1-napthyl)ethylenediamine dihydrochloride (NEDD), was purchased from Merck (India). Dubos broth base and Dubos albumin supplements were purchased from Difco (USA). Standard sterile flat-bottom 96-well plates were purchased from Tarsons (India). Fetal bovine serum (FBS) and minimum essential medium (MEM; without phenol red) were purchased from GIBCO Biosciences.

b. Bacterial Strains, Chemicals and Media

*Mycobacterium tuberculosis* H37Ra (ATCC 25177) was obtained from IMTECH, Chandigarh, India. Chemicals purchased from Sigma, USA unless mentioned. A defined medium used for our studies, containing 0.5 gm $KH_2PO_4$, 0.25 gm sodium citrate, 60 mg $MgSO_4$, 2 mM nitrite and 2 ml glycerol in 100 ml of distilled water at pH 6.6±0.2 used throughout the study. The stock cultures maintained at −70° C. and sub-cultured in liquid medium before inoculation to an experimental culture.

c. Cultivation of Aerobic and Dormant Bacilli

For aerobic cultivation, bacterial cultures were grown in 30 ml defined medium in 100 ml flask after adding inoculum size of $10^5$ cells per ml. Flask was then kept under aerobic conditions in a shaker incubator (Thermo Electron Corporation Model 481) maintained at 150 rpm and 37° C. temperature.

For cultivation of anaerobic dormant bacilli, Wayne 0.5 HSR (Head Space Ratio) model was followed in 20×125 mm tube with total volume of 25.5 ml. Inoculum size used was about $10^5$ cells per ml by diluting the culture up to 0.008 $A_{620}$. After putting 8 mm magnetic spin bar, tube was made airtight using rubber septa. The culture was gently stirred at 100 rpm on a magnetic stirrer platform. As the cells start growing, the available oxygen in air tight tube gradually got depleted, creating hypoxic condition which leads to a slow shift-down of the bacilli into dormant phase. Viable cells from aerobic and anaerobic cultures were counted on solid agar medium as described earlier. [Wayne L G, Hayes L G (1996) An in vitro model for sequential study of shiftdown of *Mycobacterium tuberculosis* through two stages of non-replicating persistence. Infect Immun 64:2062-2069].

Example 2

Estimation of Nitrate and Nitrite in Liquid Culture

Nitrate concentration in the culture was determined by a method based on salicylic acid nitration. Briefly, 50 µl of the culture was added with 200 µl of 5% salicylic acid solution prepared in conc. sulfuric acid. The solution was incubated for 20 min and 4.75 ml of 2N sodium hydroxide was added to develop yellow color. Absorbance of the sample read at 410 nm and nitrate concentration was determined by comparing standard nitrate curve.

Nitrite concentration in whole cell culture was estimated by Griess method. Briefly, 1 ml of the culture was added with 1 ml of 1% sulphanilic acid (prepared in 20% HCL) and incubated for 15 mins before addition of 1 ml of 1% naphthylenediamine dihydrochloride (NEDD) solution (prepared in DW). The tube was incubated for 15 min to develop pink color. Absorbance was measured at 540 nm and nitrite concentration was calculated by using nitrite standard curve.

For the detection of nitrite in sputum samples, same method was applied in two different formats. Firstly, 0.5 ml of sputum sample (generally mixed with saliva at different proportions) is taken in an Eppendrof tube to mixed well with 0.5 ml of reagent A and incubated for 15 minutes at room temperature. Then, 0.5 ml of reagent B is added, mixed well, incubated for 15 minutes for complete development of color.

In the second format, reagent A and B were added following the instructions mentioned above to the collection vessels directly. The color development is assessed visually and compared with a parallel set of data obtained from Chest X-Ray as well as microscopy of Acid Fast Bacilli in the same set of samples.

Example 3

THP-1 Monocytes Maintenance and Infection with *Mycobacterium tuberculosis*

THP-1 cell line maintained, routinely sub-cultured and infected with *M. tuberculosis* as follows. THP-1 cell line (ATCC® Cat. no. TIB-202™) was maintained in a 25 $cm^2$ tissue culture flask containing MEM cell culture medium with 10% heat-inactivated FBS. THP-1 cells ($5\times10^4$ cells/ml) were treated with 100 nM phorbol myristate acetate in a culture flask for 24 h to convert monocytes to macrophages. These macrophage cells were incubated for 12 h with MTBat multiplicity of infection (MOI) of 1:100 for infection.

Example 4

Quantification of mRNA Levels

To isolate total RNA, spheroplast method was applied to aerobic, hypoxia induced dormant culture and bacteria residing in macrophage. Accordingly, spheroplast solution was added to aerobically grown bacilli ($OD_{620}$~1.0), $7^{th}$ day 0.5 HSR Wayne model culture and macrophage 5th day of post infection (PI). The treated cells were used for total RNA isolation by Trizol method. 1 used for total RNA isolation bin-vitro and ex-vivo grown mycobacteria were treated with DNase-I (Sigma) and incubated at 70° C. according to manufacturers' instruction. DNase-I treated total RNA was used for cDNA synthesis using random primer and enhanced avian reverse transcriptase provided in "first strand cDNA synthesis kit" (Sigma) at 25° C. for 10 minutes followed by incubation at 45° C. for 50 minutes. The resulted cDNA was used as a template for PCR or real-time PCR amplification.

The PCR carried out as per manufacturer's instruction by using Taq DNA polymerase provided in "PCR core kit" (Sigma) in a total volume of 50 μl. Amplification product of PCR was first analyzed on 2% agarose gel containing 1% (v/v) of safe view dye followed by using NCBI blast software after nucleotide sequencing of the individual PCR product.

Real-time quantitative PCR was performed with the Brilliant SYBR Green QPCR Master Mix kit (Sigma, USA). Reactions were performed in a volume of 25 μl, and there action mixtures consisted of a 0.05 μM concentration of forward and reverse primers, 12.5 μl of 2× master mix and 2.5 μl of cDNA. The controls with no cDNA template were included in each run. Internal control for each reaction was 16S gene amplification. The PCT parameter was as follows: (i) an initial denaturation step of 2 min at 95° C., 30 sec at respective annealing temperature and 30 sec for extension at 72° C.; (iii) Final extension step of 7 min at 72° C. A melting curve analysis was then performed. All samples were run on a 2% agarose gel containing 1% (v/v) of safe view dye to verify that only a single band was produced. Each experiment was run three times by using independent RNA sample isolated from similar condition.

Example 5

Preparation of cells extract and Nir assay

For nitrite reductase enzyme assay, spheroplast solution was added to aerobically grown mycobacterial culture ($OD_{620}$~1.0) and $7^{th}$ day hypoxic Wayne tube. After incubation for 1 h, bacterial cells were pellet down using centrifugation at 10,000 rpm for 5 min at 4° C. The pellets were washed twice with potassium phosphate buffer (50 mM, pH 6.6±0.2) and resuspended in potassium phosphate buffer (50 mM, pH 7.0) containing protease inhibitor (Protease cocktail, Sigma). The prepared mixture was sonicated in water bath for 5 min at 50 kHz. The lysate was obtained after removal of un-broken cells as pellet by centrifugation at 10,000 rpm for 5 min at 4° C. The lysate was separated in another tube and was ultra-centrifuged at 100,000 rpm for 1 hr at 4° C. After centrifugation, the supernatant was again separated out in another tube while the pellet including membrane fraction was resuspended in potassium phosphate buffer containing protease inhibitor. After determining the total protein concentration of supernatant and membrane fractions using Bradford method, nitrite reductase assay was done as described by Snell et al [Bradford M M (1976) A rapid and sensitive for the quantitation of microgram quantities of protein utilizing the principle of protein-dye binding. Anal Biochem 72:248-254; Sengupta S, Melkote S, Shaila M S, Rao G R (1996) Purification and characterization of assimilatory nitrite reductase from *Candida utilis*. Biochem J 317:147-15].

Example 6

Fluorescence Microscopic Study

THP-1 macrophage cells were grown on cover slip in 8 well microplates and washed twice with chilled methanol followed by staining with 4',6-diamidino-2-phenylindole (DAPI) at final concentration of 300 nM. Macrophage cells were kept for 15 min at room temperature under dark condition. After incubation, cells were washed three times with distilled water and analyzed under the fluorescence microscope (Leitz Wetzlar model, Germany) at 350 nm excitation and 450 nm emission wavelengths (400×) using 'A' filter.

Results

1. Analysis of Nitrite Assimilation by *Mycobacterium tuberculosis* Under Aerobic and anaerobic conditions in presence of nitrate as a sole nitrogen source To analyze nitrite assimilation, MTB were grown in the culture medium containing nitrate (10 mM) as sole nitrogen source under both aerobic and anaerobic conditions. A time dependent study of nitrate utilization and nitrite release in the medium was conducted and the results are given in Table 1 below.

Table 1: Comparative nitrate utilization and nitrite release into medium by *Mycobacterium tuberculosis* grown in *M. pheli* medium containing nitrate (10 mM) as sole nitrogen source both under aerobic and anaerobic conditions.

Table 1 indicates that during active aerobic growth condition, *Mycobacterium tuberculosis* utilizes more than 7 mM of nitrite while about 3.5 mM was used during anaerobic condition. This initial study clearly shows that substantial amount of nitrite utilization takes place both under aerobic as well anaerobic conditions which may be due to functional nitrite reductase induced in presence of nitrite. Hence, *Mycobacterium tuberculosis* can grow in nitrite under different conditions.

| | Nitrate utilized (μM) | | Nitrite excreted (μM) | | Suggested Nitrite assimilated (μM) | |
|---|---|---|---|---|---|---|
| Days | $+O_2$ | $-O_2$ | $+O_2$ | $-O_2$ | $+O_2$ | $-O_2$ |
| 0 | 10000 | 10000.0 | 0 | 0 | 0 | 0 |
| 1 | 9850.01 | 9860.21 | 7.51 | 10.01 | 142.50 | 129.79 |
| 2 | 9077.58 | 9756.65 | 25.12 | 28.02 | 897.42 | 215.35 |
| 3 | 8042.50 | 8938.91 | 35.12 | 52.12 | 1922.51 | 1010.10 |
| 4 | 6307.70 | 7546.45 | 50.01 | 76.02 | 3642.30 | 2377.55 |
| 5 | 4967.51 | 6924.89 | 75.04 | 125.01 | 4957.51 | 2950.11 |
| 6 | 4142.58 | 6265.24 | 100.01 | 360.12 | 5757.42 | 3374.76 |
| 7 | 3512.52 | 5864.79 | 135.12 | 489.21 | 6352.52 | 3646.21 |
| 8 | 3037.72 | 5354.33 | 180.04 | 850.01 | 6782.28 | 3795.67 |
| 9 | 2817.61 | 5132.78 | 198.03 | 1021.02 | 6984.39 | 3846.22 |
| 10 | 2766.79 | 4993.66 | 210.02 | 1150.01 | 7023.21 | 3856.34 |

2. Growth of *Mycobacterium tuberculosis* Under Aerobic and Anaerobic Conditions in the Presence of Nitrate/Nitrite as Sole Nitrogen Source.

Mycobacerium tuberculosis bacilli were grown in defined medium with nitrite (2 mM) as a sole nitrogen source (FIG. 1*a*). It was observed that Bacilli grew well in nitrite and its growth $OD_{620}$ reached up to ~1.4 on $10^{th}$ day which is comparable with the growth curve in nitrate (10 mM). Nitrate dependent growth is positive control in this study. The nitrite assimilation occurs in a time dependent way and ~1 mM of nitrite was utilized up to $10^{th}$ day (FIG. 1*b*). The results suggest that nitrite supports the growth and its utilization in MTB during aerobic condition similar to nitrate.

Further, in another experiment, the bacilli were grown in hypoxia induced Wayne model in presence of nitrite as sole source of nitrogen. The growth curve of bacilli clearly indicates the characteristic NRP-1 and NRP-2 stages which is hall-mark of attaining dormancy in Wayne tube. The initial growth was observed in presence of nitrite for up to $5^{th}$ day after which that growth was arrested and finally a consistent $OD_{620}$~0.5 was maintained till the termination of experiment, as suggested by Wayne. It is observed that nitrite was slowly utilized in 0.5 HSR Wayne model by M. tb and nitrite utilization was continuous even at NRP-2 of its growth where bacilli growth was arrested. This indicated that nitrite can also act as alternate electron acceptor in absence of both oxygen and nitrate. The rate of nitrite utilization was ~2-fold more during actively grown culture as compared to dormant culture, which may be because of low cell count or cease in its growth in 0.5 HSR Wayne tubes.

3. Comparative Analysis of Bacterial Nitrite Reductase Operon

Analysis of nitrite reductase operon of *Mycobacterium tuberculosis* using Database of prOkaryotic OpeRons, DOOR software (csbl1.bmb.uga.edu/OperonDB/) was carried out to generate an overview of different metabolic genes localized in a specific operon. It was observed that nirB (larger, MRA_0261) and nirD (smaller, MRA_0262) subunits of nitrite reductase were localized in a same operon (ID 336089). The open reading frames (ORFs) of nirB and nirD genes revealed that the stop codon of nirB overlaps the start codon of nirD subunit, which indicated that both subunits were synthesized as a single transcript unit, similar to other prokaryotic nitrite reductase like *E. coli, Bacillus subtilis* (FIG. 2). Also nirB gene sequence of MTB H37Ra shows more than 35% similarities at protein sequence level with other prokaryotes where nitrite reductase (nirB) was well characterized. The NirB amino acid sequence was 100% identical with M tb H37Rv virulent strain while 97% and 77% with *M. bovis* BCG and *M. smegmatis* respectively (Table 2).

TABLE 2

Comparative studies of primary amino acid sequence identities of nitrite reductase larger subunit (NirB) from *Mycobacterium tuberculosis* with other organisms (Using NCBI BLAST software).

| Organisms | MTB H37Ra NirB |
|---|---|
| *S. erythraea* | 65% |
| *A. mediterranei* | 63% |
| *S. coelicolor* | 57% |
| *E. coli* | 50% |
| *B. subtilis* | 35% |
| *M. tb* H37Rv | 100% |
| *M. bovis* BCG | 99% |
| *M. smegmatis* | 77% |

Another operon (ID 3306091) named 'uroporphyrinogen operon' localized adjacent to the nitrite reductase operon, consists of two hypothetical proteins (MRA_0266, MRA_267) and a bifunctional uroporphyrinogen-III synthetase (MRA_0268). The uroporphyrinogen operon and nitrite reductase operon were suggested to be co-transcribed as uroporphyrinogen synthetase enzyme responsible for the synthesis of iron-sulfur cluster in functional nitrite reductase [Shao Z, Gao J, Ding X, Wang J, Chiao J, Zhao G (2011). Identification and functional analysis of a nitrate assimilation operon nasACKBDEF from *Amycolatopsis mediterranei* U32. Arch Microbiol 193:463-477. Layer G, Reichelt J, Jahn D, Heinz D W (2010) Structure and function of enzymes in heme biosynthesis. Protein Sci 19:1137-1161].

4. Reverse Transcriptase-PCR(RT-PCR) Study

To confirm nitrite reductase gene expression at the transcript level, RT-PCR was done using cDNA synthesized from total RNA isolated from bacilli grown in different nitrogen sources (FIG. 3). For differential expression study, specific primers were designed for nitrite reductase gene. (Primer sequences and its PCR amplification conditions mentioned in Table 3). The RT-PCR result shows nitrate reductase MRA_1172 (narG), nitrite reductase MRA_261 (nirB), and glutamine synthetase MRA_2230 (glnA1) genes were expressed when nitrate was used as a sole nitrogen source while nirB and glnA1 genes were only expressed in nitrite as a source of nitrogen. In the presence of ammonia, glnA1 was expressed. Nitrate metabolizing genes did not express in asparagine, which suggests that asparagine metabolism does not overlap nitrate metabolic pathway. Each of the PCR products confirmed the amplification of specific gene after matching the nucleotide sequence result with the available sequence in NCBI data bank. Thus, the result proved that the nirB gene represents nitrite reductase and its expression is induced specifically in presence of nitrite. Also nitrite reductase is a part of functionally active nitrate metabolic pathway in M. tb. Interestingly, the expression of all three enzymes in nitrate metabolic pathway is controlled by their substrates.

TABLE 3

Primer sequence with its annealing temperature and amplification size

| Genes | Primer sequence | Annealing temp. (° C.) | Amplification size (bp) |
|---|---|---|---|
| narG | F 5'-ACTACGCCGACAACACCAAGTTCGCCGACG-3'<br>R 5'-AGCGGCGCACATAGTCGACAAAGAACGGAA-3' | 68 | 158 |
| nirB | F 5'-GTCCCGGTTCGTTTCCTTCG-3'<br>R 5'-CGCGGGATACCAATGGACAC-3' | 68 | 155 |
| glnA | F 5'-CAACTTCTTTGTGCACGACCCGTT-3'<br>R 5'-AACTGGTAGTTGATCTCGGCCTGT-3' | 64 | 423 |
| narK2 | F5'-TGCTTCGTGATGCACCCTACTTTCGGCCCA3'<br>R5'-CCGCCGAACACGATCGCGTACAGAAACGAC3' | 68 | 120 |
| 16S* | F 5'-ATGCATGTCTTGTGGTGGAAAGCG-3'<br>R 5'-TTCACGAACAACGCGACAAACCAC-3' | 58 | 350 |

(*16S gene PCR was done for 25 cycle while PCR of other genes were done for 35 cycles)

5. Quantitative Analysis of nirB Expression at the Transcript Level

Figure 4:
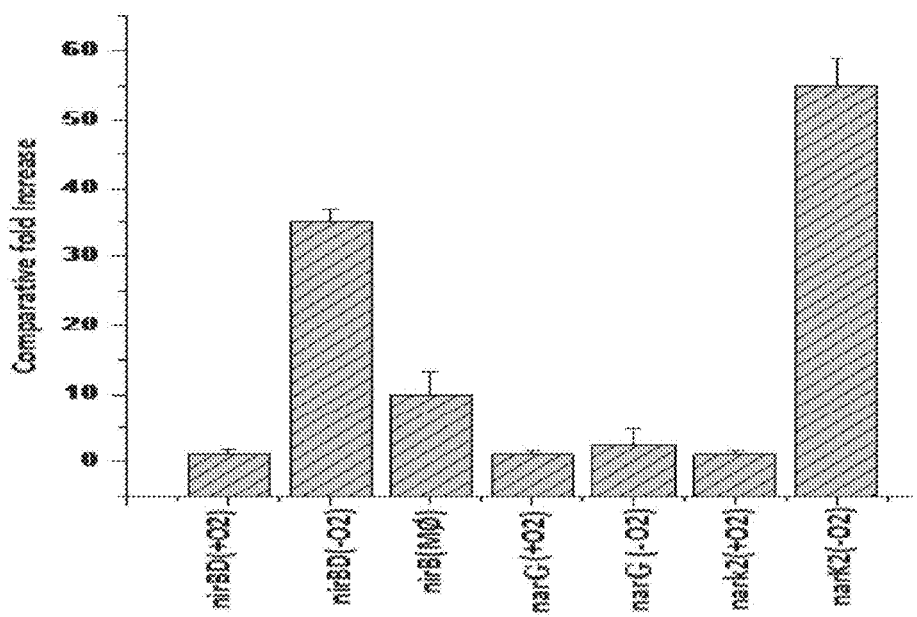
FIG. 4 shows the Real-time PCR analysis of nirB, narG and narK2 genes expression under different conditions. cDNA was prepared from the M. tuberculosis culture grown under aerobic (+O2), anaerobic (−O2) and macrophage infection model (MΦ). cDNA was used for the real-time PCR analysis using SYBR Green with gene specific primer. Relative level of the transcripts were shown as fold difference in comparison with that obtained under aerobic condition while 16S gene was used as internal control. The result shows an average of 3 identical experiments with ±SD.

Real-time PCR was used to measure the transcript level of nirB gene under aerobic, hypoxic and macrophage infection model (FIG. 4). It was observed that the level of nirB expression in bacilli under hypoxic condition is ~32 fold and macrophage infection model is ~10 fold more relative to the aerobic bacilli. The narG and narK2 genes expressions were used as positive controls for this study [Sohaskey C D, Wayne L G (2003). Role of narK2X and narGHJI in Hypoxia upregulation of Nitrate Reduction by *Mycobacterium tuberculosis*. J Bacteriol 185:7247-7256]. The results clearly indicate that nitrite reductase plays an important role during in vitrohypoxic condition and *bacillus* was dependent on nirB for its survival during dormancy. The macrophage data also suggests that nirB plays important role during survival of bacilli within the host cells.

6. Enzyme Activity of NirBD Protein

The nitrite reductase enzyme activity was quantified in MTBbacilli under different conditions (Table 4). The result indicate that the specific activity of nitrite reductase increases by ~4-fold in hypoxic cells compared to the aerobically grown cells. Nitrate reductase is chosen as marker enzyme to validate the efficient cell fractionation. The NarGHJI activity was observed only in membrane fraction as compared to cytoplasmic fraction while the nitrate reductase activity remained identical under both aerobic/hypoxic conditions which are consistent with previous report [Sohaskey C D, Wayne L G (2003) Role of narK2X and narGHJI in Hypoxia upregulation of Nitrate Reduction by *Mycobacterium tuberculosis*. J Bacteriol 185:7247-7256]. Furthermore, cells grown in presence of ammonia were taken as negative control in which no significant NirBD activity was detectable from aerobically and anaerobically grown cultures (data not shown). Interestingly, the enzyme activity was found in cytoplasmic fraction of the bacilli which was similar to the results reported from other organisms like *E. coli* [Clegg S, Yu F, Griffiths L, Cole J A (2002). The roles of the polytopic membrane proteins NarK, NarU and NirC in *Escherichia coli* K-12: two nitrate and three nitrite transporters. Mol Microbiol 44:143-15527]. Furthermore, increased specific activity of NirBD during hypoxic condition also supports the increased level of nirB mRNA at transcript level.

TABLE 4

Specific activities of nitrate reductase and nitrite reductase enzymes in cytoplasm and membrane fraction

| | Sp. activity of enzyme ±SD (U/mg of protein)* | |
|---|---|---|
| MTB | Cytoplasm | Membrane |
| NR (+$O_2$) | 0.5 (±0.009) | 12.0 (±0.48) |
| NR (−$O_2$) | 0.8 (±0.023) | 9.52 (±3.8) |
| Nir (+$O_2$) | 6.02 (±0.16) | 0.42 (±0.022) |
| Nir (−$O_2$) | 24.45 (±0.52) | 0.96 (±0.042) |

MTB cells were grown in presence of nitrate/nitrite as nitrogen source in *M. pheli* medium and specific enzyme activity was measured on mid-logarithmic phase for aerobic (+$O_2$) and on 7th day hypoxia induced Wayne model (−$O_2$) culture after lysis of cells by spheroplast method as mentioned in Material and Method". Total protein was quantified by Bradford method using BSA as standard protein. *1 Unit of specific activity of enzyme was defined as 1 μM of $NO_2^-$ (μM) produced or utilized during NR or NirB enzyme assay per min/mg of total protein.

7. Effect of Nitrite Reductase Inhibitor [para-hydroxy mercuric benzoate (p-HMB)] on Bacilli Grown in Aerobic, Anaerobic and within THP-1 Macrophages.

Figure 5:
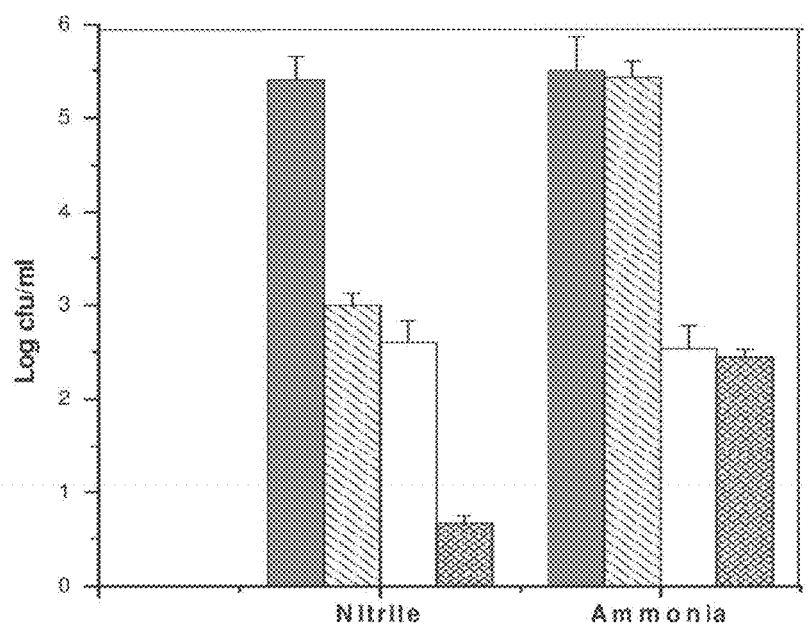
FIG. 5 shows the effect of p-Hydroxy Mercuric Benzoate (p-HMB) on the viability of active and dormant bacilli grown in minimal medium containing nitrite or ammonia as a sole nitrogen source. Dark bars represent aerobic condition without inhibitor, spotted bars represent aerobic condition with p-HMB (100 μM), light bars: anaerobic dormant condition without inhibitor, Crossed spotted bar: anaerobic dormant with inhibitor.

The inhibitor para-hydroxy mercuric benzoate (p-HMB) at final concentration of 100 μM (prepared in DW) was added at the time of inoculation of cultures and cell counts were carried out on $10^{th}$ day. It was observed that p-HMB kills bacilli grown in nitrite as sole nitrogen source under aerobic and 0.5 HSR Wayne tube dormant cultures (FIG. 5). The cell count reduced by ~2.5 log difference as compared to bacilli grown under ammonia, where no inhibition was observed in presence of p-HMB. The results indicate that p-HMB is specifically inhibiting nitrite reductase and blocks the nitrate metabolic pathway which is effective under both aerobic and hypoxia induced dormant conditions (FIG. 5).

Figure 6:
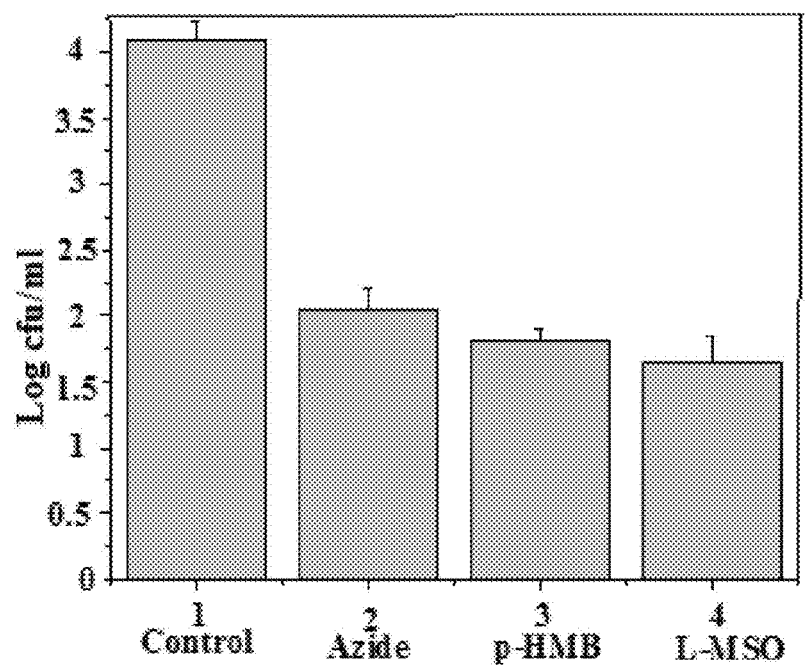
FIG. 6 shows the effect of nitrate reduction pathway inhibition on the growth and survival of M. tuberculosis in THP-1 macrophage. 100 μM each of Azide as nitrate reductase, p-HMB as nitrite reductase and L-MSO as glutamine synthetase inhibitors respectively was added at the time of inoculation and effect on growth was examined by lysis the THP-1 macrophage at 10th say of PI and the cfu count was compared with control (without any inhibitor). The experiments were carried out three times and results are the means±SD.
Figure 7:
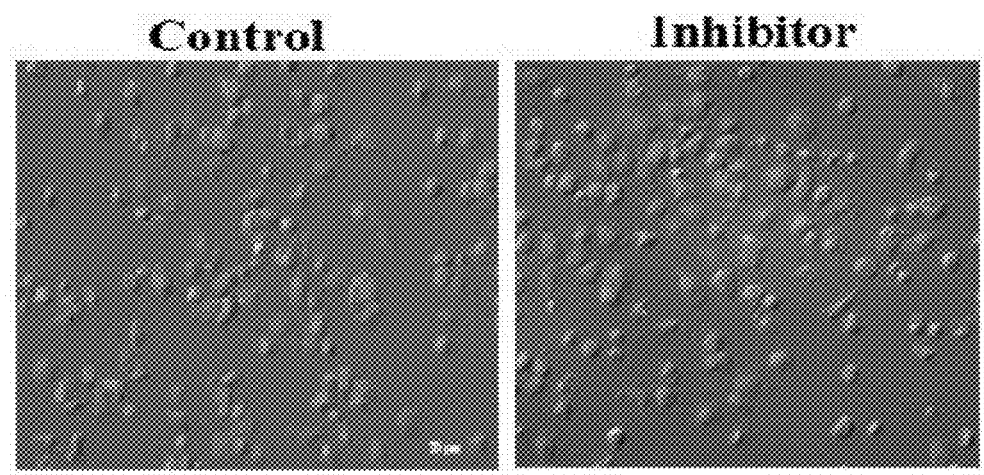
FIG. 7 shows the effect of p-HMB inhibitor on THP-1 macrophages. The THP1 macrophages were treated with 100 μM of p-HMB (Inhibitor) and incubated for 10 days and then stained with DAPI dye before taking pictures under a fluorescent microscope. The control cells were treated with the vehicle only under identical conditions.

Further, p-HMB inhibitor was added for nitrate reductase, nitrite reductase and glutamine synthetase enzyme separately at zero day of post-infection (PI) and cell counts were taken on $10^{th}$ day of PI (FIG. 6). p-HMB inhibits the intracellular bacilli count by ~2 log difference compared to control (without inhibitor). Azide and L-methionine sulfoximine (L-MSO) which are specific inhibitors of nitrate reductase and glutamine synthetase respectively showed decrease in viable cell count by ~1.5 and ~2.5 log difference compared with the control. The study indicates that nitrite reductase is an equally important enzyme for the survival of bacilli within macrophage as nitrate reductase and glutamine synthetase.

8. Cytotoxic Effect of Para-Hydroxy Mercuric Benzoate (p-HMB) on THP-1 Macrophages To investigate the host THP-1 macrophage cells condition due to its exposure to p-HMB inhibitor before considering its effective and specific inhibition of bacilli in macrophage infection models, fluorescence microscopic picture of THP-1 cells treated with p-HMB (100 μM) was compared with the untreated control after staining with DAPI (4',6-diamidino-2-phenylindole). Fluorescence images were taken after $10^{th}$ day of inhibitor treatment. The results showed that the integrity and compactness of nuclear structure was similar to the normal ones, indicating the healthy state of the host cells similar to untreated control. This study indicated the specific effect of inhibitor on mycobacteria growing within macrophage without exhibiting any cytotoxic effects on macrophage.

9. Assessment and Standardization of Different Methods to Test the Usability of Nitrite as Biomarker in Various Patient Samples in Simulated Environment for the Detection and Estimation of Tubercle Bacilli in Humans Samples Sputum acid fast bacilli is a useful primary diagnostic tool for rapid detection of TB cases, however, acid fast bacilli smear-based diagnosis can miss half of the cases at first presentation (Seema Irfan, Rumina Hasan, Akber Kanji, Qaiser Hassan, Iqbal Azam (2008), Infectious Diseases Journal of Pakistan, 17 (01); 10-13). There are reports which suggested that overall diagnostic sensitivity of direct Zeihl Neelsen smear remained disappointing in resource poor settings (David Wilkinson and A. Wim Sturm (1997). Trans. Royal Soc. Exp. Med. Hyg. 91 (4); 420-421). Initially, blood and urine samples were collected from hospitals for carrying out the investigation for detecting presence of nitrite in clinical samples.

A. Blood Samples collected from Medipoint hospital at Aundh, Pune, India (Tested July-August 2012)

1) Fresh blood sample: From vein to tube (no coagulant)
Reasoning: Nitrite might be unstable in blood
Samples tested: 2 (identical condition)
Outcome: not suitable as coagulation and improper settlement of RBC debris interfares with color detection.

2) Blood samples from hospitals, collected with or without different coagulants (colour coded caps)
Reasoning: Different coagulants may have different interaction with the color detection reagents
Samples tested: 5 (1 sample each for each color codes, purple cap, 2 samples)
Parameters tested: 4 different cap-color code, natural settling of RBC vs. centrifugation, with or w/o nitrite, order of addition of reagents A and B with and w/out centrifugation in between.
Total tests done: 14
Outcome: Red cap or Purple caps needs to be optimized, others are useless.

3) Blood samples from hospital, collected with or without different coagulants (red and purple caps only)
Samples tested: 4 (2 for each cap color)
Parameters used: With vs. without nitrite, addition of A followed by centrifugation, addition of A and B both followed by centrifugation.
Total tests done: 16
Outcome: Blood collected in purple cap tube gives better color detection if centrifugation is performed after addition of A 4) Blood samples from hospital, collected in purple cap tubes
Sample tested: 1
Parameters used: with vs. without nitrite, usage of 1× volume of A and B vs. usage of 4× volume of A and B
Total tests done: 8
Outcome: Best protocol for better color detection is
Add 4× volume of A, incubate for at least 5 minutes, centrifuge
Add B, centrifuge again, check supernatant for color.

5) Blood samples from hospital, collected in purple cap tubes
Samples tested: 2
Parameters used: with vs. without nitrite, incubation with A for 15', 30', 1 hr and 2 hr
Total tests done 16
Reasoning: Addition of A freezes nitrite, so if A is added right away, and centrifuged after quite some time, it simulates the condition, when the sample needs to be transported (from hospitals lacking centrifugation facility), to a distance of 15 min to 2 hr for further analysis.
Results: Timing of B addition do not have much effect, and if nitrite is present, the patient sample can be analyzed safely even after transportation.

Summary of Blood Sample Testing Protocols:
No. of tests done: 56
Conclusion: If blood is collected in EDTA coated tube, A and B reagents can detect 80 μM nitrite in blood spiked with nitrite (post collection), and the standardized method is method no. 5.

B. Urine Samples (Tested July-December 2012)
1) Urine samples from hospital
Samples tested: 2
1 +veUTI, 1 −ve, needed nitrite spiking to see color, −ve sample became deep blue in the next day
2) Urine samples from hospital
Samples tested: 5
All −ve, became blue with different shades in the next day
3) Urine samples from hospital
Samples tested: 2
1 +veUTI, 1 −ve, needed nitrite spiking to see color
4) UTI patient's urine sample from hospital
Sample tested 1
No color developed
Summary:
Total no. of tests=10
Conclusion: probably need true culture positive patients for proper evaluation of these samples.

C. Sputum Samples
Sputum sample were collected in Pune Chest Hospital, Aundh. All samples were collected on the basis of past history of a) coughing for longer period, b) weight loss and c) insensitivity to standard antibiotics. At Pune Chest Hospital, Aundh, Pune all the patients were screened for chest X-ray as well as sputum for microscopy of acid fast bacilli in smears. The microscopic data also provided in standard formats as follows:
0 Acid fast bacilli/100 fields which means: negative
1-9 Acid fast bacilli/100 fields which means: actual number of bacilli seen on whole slide
10-99 Acid fast bacilli/100 fields: 1+
1-10 Acid fast bacilli/field in 50 fields:2+
>10 Acid fast bacilli/field in 20 fields: 3+
All the testing with sputum samples was done with suspected TB patient samples collected in the hospital. The result is shown in Table 4

Table 5
Two methods were used:
i) 100 μl of sputum was transferred to a small Eppendorf tube and reagents A and B were added (similar to the methods used for blood and urine analysis and described earlier in detail).
ii) Reagents A and B were sequentially added to the cups containing patients' sputum.
iii) The color was monitored as well as recorded by taking snap pictures using a digital camera. So, the actual color of the reaction mixture is recorded.
iv) The color was analyzed respect to the parallel set of data (from Chest X-ray and microscopy of Acid Fast Bacilli) obtained by competent. Hospital technicians on the same sample.

D. Identification of Suitable Sample for TB Diagnostic Study

Generally, patients with cough for 3 weeks or longer, weight loss and no antibiotic response was screened for chest X-ray as well as microscopy of sputum samples. While testing of nitrite in these sputum samples from suspected TB patients, it was found that blood samples from the same patient are rarely withdrawn. Still, for one patient, both blood and sputum were available. The sputum test was positive, blood test was negative.

| S. No. | Date Of Testing | OPD/ IPD | APB (Microscopy) | Result | Color | Patient History | X-Ray report | Admission Date | Present status | Assay Volume N (no.) |
|---|---|---|---|---|---|---|---|---|---|---|
| 1 | 24 Sept. 2012 | IPD | +Ve | +Ve | Deep Purple Color | ICS (HIV +ve) | Δ PTB | 20 Sept. 2012 | Expired 26 Sept. 2012 | Whole Cup n1 |
| 2 | 24 Sept. 2012 | IPD | +Ve | +Ve | Deep Purple Color | Cat II | PTB | 20 Sept. 2012 | Discharged 27 Sept. 2012 | Whole Cup n1 |
| 3 | 28 Sept. 2012 | IPD | −Ve | −Ve | No Color | | PTB | 26 Sept. 2012 | Discharged 4 Oct. 2012 | 100 ul n1 |
| 4 | 28 Sept. 2012 | IPD | −Ve | +Ve | Purple | | PTB | 26 Sept. 2012 | DAMA 19 Oct. 2012 | 100 ul n1 |
| 5 | 28 Sept. 2012 | Civil OPD | −Ve | +Ve | Purple | | | | | 100 ul n1 |
| 6 | 3 Oct. 2012 | IPD | +1 | −Ve | No Color | Cat I | Miliary (over infection) PTB | 1 Oct. 2012 | Discharged 8 Oct. 2012 | 100 ul n1 |
| 7 | 3 Oct. 2012 | IPD | +1 | −Ve | No Color | ICS, Cat II, psychic/ epilepsy/ paralysis | Miliary | 1 Oct. 2012 | Referred to Sassoon | 100 ul n1 |
| 8 | 3 Oct. 2012 | IPD | −Ve | −Ve | No Color | | PTB | 2 Oct. 2012 | Admitted | 100 ul n1 |
| 9 | 3 Oct. 2012 | IPD | −Ve | +Ve | Pink | | PTB? | 1 Oct. 2012 | Discharged 3 Oct. 2012 | 100 ul n1 |
| 10 | 3 Oct. 2012 | IPD | −Ve | −Ve | No Color | | PTB | 26 Sept. 2012 | Discharged 4 Oct. 2012 | 100 ul n1 |
| 11 | 3 Oct. 2012 | OPD | −Ve | +Ve | Light Pink | | | | | 100 ul n1 |
| 12 | 3 Oct. 2012 | OPD | +3 | −Ve | No Color | | PTB | 4 Oct. 2012 | Admitted | 100 ul n1 |
| 13 | 3 Oct. 2012 | OPD | −Ve | −Ve | No Color | | | | | 100 ul n1 |
| 14 | 4 Oct. 2012 | IPD | +3 | −Ve | No | Transfer to MDR ward, Cat I, readmitted as Cat IV on 11 Dec. 2012 | Pulmonary Kochys | 3 Oct. 2012 | Rifampicin & INH resistant. | 100 ul n2 |
| 15 | 4 Oct. 2012 | IPD | −Ve | −Ve | No Color | | | | | 100 ul n2 |
| 16 | 4 Oct. 2012 | IPD | −Ve | −Ve | No Color Turbid | | | | | 100 ul n2 |
| 17 | 4 Oct. 2012 | IPD | −Ve | +Ve | Purple (1 OD) | | | | | 100 ul n2 |
| 18 | 4 Oct. 2012 | IPD | −Ve | +Ve | Purple (1 OD) | | | | | 100 ul n2 |
| 19 | 4 Oct. 2012 | TB OPD | −Ve | +Ve | Light Pink | | | | | 100 ul n2 |
| 20 | 4 Oct. 2012 | Civil OPD | +1 | +Ve | Pink | | | | | 100 ul n2 |
| 21 | 4 Oct. 2012 | TB OPD | −Ve | −Ve | No Color | | | | | 100 ul n2 |
| 22 | 4 Oct. 2012 | TB OPD | −Ve | −Ve | No Color Turbid | | | | | 100 ul n2 |

-continued

| S. No. | Date Of Testing | OPD/ IPD | APB (Micro-scopy) | Result | Color | Patient History | X-Ray report | Admission Date | Present status | Assay Volume N (no.) |
|---|---|---|---|---|---|---|---|---|---|---|
| 23 | 5 Oct. 2012 | IPD | −Ve | −Ve | No Color | AFB S2 S2 on 8 Oct. 2012 | | 4 Oct. 2012 | Discharged 6 Nov. 2012 6 Nov. 2012 | Whole Cup n2 |
| 24 | 5 Oct. 2012 | IPD | 1+ | +Ve | Dark Purple, >1 OD | Culture Done. HIV -Ve, since 5 months taking medicines without cure, continuous fever | Over infection PTB later MDR | 4 Oct. 2012 | Expired 30 Oct. 2012 | Whole Cup n2 |
| 25 | 5 Oct. 2012 | IPD | S2 S4 | +Ve | Dark Purple, >1 OD | | PTB | 4 Oct. 2012 | Discharged 16 Oct. 2012 | Whole Cup n1 |
| 26 | 5 Oct. 2012 | IPD | 1+ | +Ve | Pink <0.5 OD | | PTB | 4 Oct. 2012 | Expired 31 Oct. 2012 | Whole Cup n1 |
| 27 | 5 Oct. 2012 | IPD | 3+ | +Ve | Light Pink | | PTB | 28 Sept. 2012 | Discharged Physically 9 Oct. 2012 | Whole Cup n2 |
| 28 | 11 Oct. 2012 | 1, 2, 3 Wd | −Ve | +Ve | Dark Purple, >1 OD | | Δ PTB | 10 Oct. 2012 | Expired 16 Oct. 2012 | 100 ul n2 |
| 29 | 11 Oct. 2012 | 1, 2, 3 Wd | −Ve | −Ve | No Color | Cat II | | 21 Jul. 2012 | Admitted | 100 ul n2 |
| 30 | 11 Oct. 2012 | MMW 101 | −Ve | +Ve | Dark Purple, >1 OD | | | | | 100 ul n2 |
| 31 | 11 Oct. 2012 | PCH OPD | −Ve | −Ve | No Color | | | | | 100 ul n2 |
| 32 | 11 Oct. 2012 | Civil IPD | −Ve | +Ve | Light Pink | | | | | 100 ul n2 |
| 33 | 11 Oct. 2012 | PCH OPD | −Ve | +Ve | Dark Purple, >1 OD | | | | | 100 ul n2 |
| 34 | 12 Oct. 2012 | IPD | −Ve | +Ve | Purple | | | | | Whole Cup n1 |
| 35 | 12 Oct. 2012 | MMW | −Ve | +Ve | Dark Purple, >1 OD | | | | | Whole Cup n2 |
| 36 | 12 Oct. 2012 | Isolation | −Ve | +Ve | Very Light Pink | | | | | Whole Cup n1 |
| 37 | 12 Oct. 2012 | OPD | −Ve | +Ve | Both Light Pink | | | | | Whole Cup n2 |
| 38 | 12 Oct. 2012 | OPD | 1+ | +Ve | Dark Purple, >1 OD | | | | | Whole Cup n1 |
| 39 | 12 Oct. 2012 | OPD | −Ve | -Ve | No Color | | | | | Whole Cup n2 |
| 40 | 12 Oct. 2012 | OPD | −Ve | +Ve | Purple | | | | | Whole Cupn1 |
| 41 | 13 Oct. 2012 | PCH OPD | −Ve | −Ve | No Color | | | | | Whole Cup n2 |
| 42 | 13 Oct. 2012 | PCH OPD | 2+ | −Ve? | No Color (Pinkish Turbidity) | Cat II | PTB Relapsed | 13 Oct. 2012 | Discharged 30 Nov. 2012 | Whole Cup n2 |
| 43 | 13 Oct. 2012 | Civil OPD | −Ve | −Ve | No Color | | | | | Whole Cup n2 |
| 44 | 13 Oct. 2012 | PCH OPD | −Ve | +Ve | Dark Purple, >1 OD | | | | | Whole Cup n1 |
| 45 | 13 Oct. 2012 | PCH OPD | +Ve | +Ve | Magenta, 1 OD | | PTB | 12 Oct. 2012 | Discharged 13 Nov. 2012 | Whole Cup n1 |
| 46 | 13 Oct. 2012 | PCH OPD | −Ve | +Ve | Light Pink | | | | | Whole Cup n2 |
| 47 | 13 Oct. 2012 | PCH OPD | 1+ S3 | +Ve | Pale Pink No color | | | | | Whole Cup n2 |

-continued

| S. No. | Date Of Testing | OPD/ IPD | APB (Microscopy) | Result | Color | Patient History | X-Ray report | Admission Date | Present status | Assay Volume N (no.) |
|---|---|---|---|---|---|---|---|---|---|---|
| 48 | 13 Oct. 2012 | PCH OPD | −Ve | +Ve | Light Magenta | | | | | Whole Cup n1 |
| 49 | 13 Oct. 2012 | PCH OPD | −Ve | +Ve | Magenta | | | | | Whole Cup n1 |
| 50 | 17 Oct. 2012 | Civil OPD | −Ve | −Ve | Both No Color | | | | | Whole Cup n2 |
| 51 | 17 Oct. 2012 | PCH OPD | 1+ 1+ | −Ve | Both No Color | | | | | Whole Cup n2 |
| 52 | 17 Oct. 2012 | PCH OPD | 1+ 1+ | +Ve | −Ve Magenta | | | | | Whole Cup n2 |
| 53 | 17 Oct. 2012 | 1, 2, 3 ward | 3+ 3+ | +Ve | Pale Pink Pink | | Δ PTB | 16 Oct. 2012 | Transfer To MDR on 22 Oct. 2012 | Whole Cup n2 |
| 54 | 17 Oct. 2012 | 1,2,3 ward | −Ve | +Ve | Pink Tinge No Color | Cat I | Δ PTB | 15 Oct. 2012 | Discharged 25 Oct. 2012 | Whole Cup n2 |
| 55 | 17 Oct. 2012 | PCH OPD | 1+ 1+ | +Ve | Both Pink | Cat I then Cat II | PTB | 16 Oct. 2012 | Discharged 22 Oct. 2012 | Whole Cup n2 |
| 56 | 17 Oct. 2012 | PCH OPD | −Ve | −Ve | No Color | | | | | Whole Cup n2 |
| 57 | 19 Oct. 2012 | PCH IPD (wd | 1+ 1+ | −Ve | Both No Color | Cat II, MDR | PTB | 28 Jun. 2012 | Extension | Whole Cup n2 |
| 58 | 19 Oct. 2012 | PCH IPD (wd | −Ve | +Ve | Both Purple | | PTB | 18 Oct. 2012 | Discharged 22 Oct. 2012 | Whole Cup n2 |
| 59 | 19 Oct. 2012 | PCH IPD (wd 1,2,3) | −Ve −Ve | −Ve | Both No Colour | | PTB | 18 Oct. 2012 | DAMA 25 Oct. 2012 | Whole Cup n2 |
| 60 | 19 Oct. 2012 | Civil IPD | −Ve | +Ve −Ve | Both Pink/Yellow | | | | | Whole Cup n2 |
| 61 | 19 Oct. 2012 | Civil IPD (ICU 108) | −Ve | +Ve | No Color Light Pink | | | | | Whole Cup n2 |
| 62 | 19 Oct. 2012 | ISO 107 | −Ve | −Ve | No Color | | | | | Whole Cup n1 |
| 63 | 19 Oct. 2012 | PCH OPD | −Ve | +Ve | No Color Dark | | | | | Whole Cup n2 |
| 64 | 19 Oct. 2012 | MMW 101 | 1+ 1+ | +Ve | No Color Dark Purple, >1 OD | Transfer from AGH | | 7 Dec. 2012 | Expired 7 Dec. 2012 | Whole Cup n2 |
| 65 | 27 Oct. 2012 | PCH OPD | S3 −Ve | −Ve | Both No Color | | | | | Whole Cup n2 |
| 66 | 27 Oct. 2012 | PCH OPD | S5 S8 | −Ve | Both No Color | | | | | Whole Cup n2 |
| 67 | 27 Oct. 2012 | WD 1, 2, 3 | −Ve | +Ve | Both Pale Pink | Cat I | PTB | 25 Oct. 2012 | Discharged 29 Oct. 2012 | Whole Cup n2 |
| 68 | 6 Dec. 2012 | PCH OPD | 1+ 1+ | +Ve | No Color Pink | | | | | Whole Cup n2 |
| 69 | 6 Dec. 2012 | AGH 7899 | −Ve | +Ve | No Color Pale | | | | | Whole Cup n2 |
| 70 | 6 Dec. 2012 | PCH OPD | −Ve | −Ve | Both No Color | | | | | Whole Cup n2 |
| 71 | 6 Dec. 2012 | PCH 1, 2, 3 | −Ve | +Ve | Magenta Pale ICS | ICS | PTB | 5 Dec. 2012 | Discharged | Whole Cup n2 |
| 72 | 6 Dec. 2012 | PCH OPD | −Ve | +Ve | Dark Magenta Pink | | | | | Whole Cup n2 |

-continued

| S. No. | Date Of Testing | OPD/ IPD | APB (Microscopy) | Result | Color | Patient History | X-Ray report | Admission Date | Present status | Assay Volume N (no.) |
|---|---|---|---|---|---|---|---|---|---|---|
| 73 | 6 Dec. 2012 | AGH OPD | −Ve | −Ve | No Color | | | | | Whole Cup n1 |
| 74 | 6 Dec. 2012 | PCH OPD | 1+ −Ve | +Ve | Magenta | | | | | Whole Cup n1 |
| 75 | 6 Dec. 2012 | PCH OPD | 1+ 1+ | +Ve | Both Pink | | | | | Whole Cup n2 |
| 76 | 6 Dec. 2012 | | not done | +Ve | Pale Magenta | | | | | Whole Cup n2 |
| 77 | 8 Dec. 2012 | PCH OPD | 1+ 1+ | +Ve | No Color Pale Pink | | | | | Whole Cup n2 |
| 78 | 8 Dec. 2012 | PCH OPD | −Ve | +Ve | Both Magenta | | | | | Whole Cup n2 |
| 79 | 8 Dec. 2012 | PCH 1295 | −Ve | +Ve | Light Pink Magenta | | | | | Whole Cup n2 |
| 80 | 8 Dec. 2012 | PCH OPD | −Ve | +Ve | Magenta | Epithelial malignancy (Scalp) Surgery One & half years ago | Consolidatiion | 7 Dec. 2012 | Referred to Sassoon 11 Dec. 2012 | Whole Cup n1 |
| 81 | 8 Dec. 2012 | PCH | 2+ 2+ | −Ve | No Color | | PTB | 7 Dec. 2012 | Expired | Whole Cup n2 |
| 82 | 8 Dec. 2012 | AGH OPD | −Ve | +Ve | Magenta | | | | | Whole Cup n1 |
| 83 | 8 Dec. 2012 | PCH OPD | −Ve | −Ve | No Color | | | | | Whole Cup n2 |
| 84 | 12 Dec. 2012 | PCH OPD | −Ve | −Ve | No Color | | | | | Whole Cup n2 |
| 85 | 12 Dec. 2012 | MMW1 01 | 3+ 3+ | +Ve | Pink Magenta | | | | | Whole Cup n2 |
| 86 | 12 Dec. 2012 | PCH OPD | −Ve | +Ve | Pale Pink | | | | | Whole Cup n2 |
| 87 | 12 Dec. 2012 | PCH OPD | −Ve | +Ve | -Ve Magenta | | | | | Whole Cup n2 |
| 88 | 12 Dec. 2012 | PCH OPD | S5 S3 | +Ve | -Ve Pink | | | 18 Dec. 2012 | | Whole Cup n2 |
| 89 | 15 Dec. 2012 | MMW 101 | −Ve | +Ve | Magenta Light Pink | | | | | Whole Cup n2 |
| 90 | 15 Dec. 2012 | 1, 2, 3 Ward | 3+ 3+ | +Ve | Purple Pink | | | | | Whole Cup n2 |
| 91 | 15 Dec. 2012 | 1, 2, 3 Ward | 1+ 1+ | +Ve | Dark Purple | | | | | Whole Cup n1 |
| 92 | 15 Dec. 2012 | PCH OPD | 3+ 3+ | +Ve | Pink -Ve | | | | | Whole Cup n2 |
| 93 | 18 Dec. 2012 | 1, 2, 3 Ward | 1+ | +Ve | Pale Pink above | | | | | Whole Cup n2 |
| 94 | 18 Dec. 2012 | 1, 2, 3 Ward | 1+ | +Ve | Pale Pink above | | | | | Whole Cup n2 |
| 95 | 18 Dec. 2012 | 1, 2, 3 Ward | −Ve | +Ve | Purple | | | | | Whole Cup n1 |
| 96 | 18 Dec. 2012 | PCH OPD | 1+ | +Ve | Magenta | | | | | Whole Cup n1 |
| 97 | 18 Dec. 2012 | AGH OPD | −Ve | +Ve | Light Pink Pink | | | | | Whole Cup n1 |
| 98 | 18 Dec. 2012 | PCH OPD | S4 S7 | −Ve | No color | | | | | Whole Cup n1 |
| 99 | 18 Dec. 2012 | ICTC | −Ve | +Ve | Pink | | | | | Whole Cup n1 |
| 100 | 18 Dec. 2012 | AGH OPD | −Ve | −Ve | No color | | | | | Whole Cup n 2 |
| 101 | 18 Dec. 2012 | AGH OPD | −Ve | +Ve | Magenta | | | | | Whole Cup n1 |
| 102 | 18 Dec. 2012 | PCH OPD | −Ve | +Ve | Purple | | | | | Whole Cup n1 |

Conclusion: Sputum should be used for testing pulmonary TB cases.

E. Sputum test report Table 5

Total 101 samples were tested by the present method with 66 in duplicate and 2 samples repeated. 49 results matched with AFB data of which 24 were positives and 21 were negatives. 4 of them who expired developed purple/dark pink color after adding reagent to sputum samples which clearly indicated heavy bacilli burden in patient's body. One of them was carrying MDR bacilli.

Out of 21 negatives, 4 were discharged (1 DAMA, 3 were PTB 1 was AFB +Ve when repeated), 2 were receiving treatment for almost 3 to 5 months.

Out of 101 cases only, 3 sputum samples were scored as just positive.

The result clearly shows that 22 cases out of 102 were found to be negative both by microscopy as well as nitrite detection.

Out of 102 samples, 20 got 1+ score in microscopy but 4 cases were found to be negative, 4 pale pink, 5 pink, 4 dark purple (2 expired), 3 magenta.

Only 2 samples were scored as 2+ but both were detected as negative in our method.

6 samples were scored as +3, 2 no color and 1 each of light pink, pale pink, pink, purple and magenta.

Most interestingly, 41 AFB negative samples were positive by the present method. 1 of them expired and was identified from Purple color as carrying heavy burden of the bacilli. Most of them were diagnosed as PTB positive patients from their chest X-ray report.

11 AFB positive samples were identified as negative by our method. Out of which 1 patient expired and 3 patients still admitted, 1 carrying MDR TB.

Morning samples were found to develop relatively better color compared to the evening sputum samples.

Overall, intensity of the color in nitrite detection of the sputum samples is found to be well correlated with the severity of the disease. However, the performance of the so called standard methods remained disappointing particularly in this study carried out at Pune Chest Hospital, Aundh.

The results of sputum testing are given below:

| Abbreviations | |
|---|---|
| +Ve +Ve; –Ve –Ve | Results matched |
| –Ve +Ve | AFB negatives, Our method detected positive |
| +Ve –Ve | AFB positives, Our method detected negative |
| 100 ul | Lesser Volume used for the experiment |
| Sudhir Mane, Sonali Bobde | Samples Repeated |
| +Ve | Positive |
| –Ve | Negative |
| DAMA | Discharged Against Medical Advice |
| PTB | Pulmonary TB |

Conclusion
1. Out of 102 samples 42 results did not match.
2. Out of 102 samples, result of 49 samples matched with microscopic data and 2 samples were repeat testing of same patient.
3. The number of positive samples (68) detected by our method is almost double than the microscopic (37) method but 11 of it did not match.
4. Saliva is an advantage.
5. MDR also have color.
6. Patient expiry more related to dark purple/Magenta color which clearly suggests that the patients were heavily infected with the bacilli.
7. Adding reagents in the sputum collection cup is more simple and reliable.

Advantages
1. The method facilitates identification of active and dormant stage inhibitors of *Mycobacterium tuberculosis*.
2. The diagnostic method is an efficient method to detect increase or decrease of bacilli even after the treatment has started.
3. Intensity of the color in nitrite detection of the sputum samples is found to be well correlated with the severity of the disease.
4. The drug identified will work on bacilli present in a complex medium like our body fluids where all the N2 sources will be present and the inhibitor will kill it. So, its importance is validated in macrophage or our body. We have shown that inhibitor of nitrite reductase works in macrophage.
5. The method concluded the nitrite reductase activity under hypoxia, 2) within macrophage and 3) seen inhibition only under hypoxic condition as well as within macrophage at a stage of advanced growth.

I claim:

1. A method for screening inhibitors against nitrite reductase useful as anti-tubercular drug comprising:

i. infecting Thp1 macrophage culture in wells of a plate with *Mycobacterium tuberculosis;* ii. washing the infected macrophage culture with 1×PBS solution followed by adding fresh medium containing 50 mM of sodium nitrate;

iii. adding 2.5 µl of a test inhibitor(s) against nitrite reductase in DMSO to the infected macrophage culture in a well of the plate on 0 d;

iv. adding 2.5 µl of one or more standard inhibitors of narG, nirB and glnA1 at their respective $IC_{90}$ to the infected macrophage culture in separate wells of the plate on 5 d and incubating the plate for nearly 8 d;

v. estimating the level of ammonia/nitrite in the culture medium for determining the viable cell count; and vi. determining reduction in the viable cell count by the test inhibitor(s) as compared to the standard inhibitor(s) to obtain an anti-tubercular drug target.

2. The method as claimed in claim 1 wherein the inhibitors against nitrite reductase are selected from the group comprising of enzymes belonging to nitrate metabolic pathway that kill dormant/latent *Mycobacterium tuberculosis* (MTB) bacilli.

3. The method as claimed in claim 2 wherein the inhibitors against nitrite reductase are selected from the group comprising of rifampicin, pentachlorophenol, streptomycin, isoniazid, ethambutol, pyrazinamide.

4. The method as claimed in claim 1 wherein the inhibitors against nitrite reductase are against active and dormant stage of *Mycobacterium tuberculosis.*

5. The method as claimed in claim 1 wherein the *bacillus* is under aerobic, hypoxia induced dormancy and in Human acute monocyte leukemia cell line Thp1 macrophages.

6. A method of treating *Mycobacterium tuberculosis* comprising administering to a subject in need thereof one or more of the inhibitors against nitrite reductase as claimed in claim 1.

* * * * *